(12) United States Patent
Kreidler et al.

(10) Patent No.: US 11,653,928 B2
(45) Date of Patent: May 23, 2023

(54) DEVICE FOR ATRIAL APPENDAGE EXCLUSION

(71) Applicant: DATASCOPE CORP., Fairfield, NJ (US)

(72) Inventors: Marc Kreidler, Sunnyvale, CA (US); Juan Perez, San Jose, CA (US); Joseph Lamberti, Castro Valley, CA (US); Ashik Mohan, Alamo, CA (US)

(73) Assignee: DATASCOPE CORP., Wayne, NJ (US)

( * ) Notice: Subject to any disclaimer, the term of this patent is extended or adjusted under 35 U.S.C. 154(b) by 617 days.

(21) Appl. No.: 16/366,738

(22) Filed: Mar. 27, 2019

(65) Prior Publication Data

US 2019/0298381 A1 Oct. 3, 2019

Related U.S. Application Data

(60) Provisional application No. 62/649,455, filed on Mar. 28, 2018.

(51) Int. Cl.
*A61B 17/12* (2006.01)
*A61B 17/122* (2006.01)
(Continued)

(52) U.S. Cl.
CPC ...... *A61B 17/12122* (2013.01); *A61B 17/064* (2013.01); *A61B 17/068* (2013.01);
(Continued)

(58) Field of Classification Search
CPC ............ A61B 17/12122; A61B 17/122; A61B 17/064; A61B 17/068; A61B 2017/1205;
(Continued)

(56) References Cited

U.S. PATENT DOCUMENTS

| 729,116 A | 5/1903 | Barnstead |
| 1,756,670 A | 4/1930 | Treat |

(Continued)

FOREIGN PATENT DOCUMENTS

| CN | 1864642 A | 11/2006 |
| CN | 1883411 A | 12/2006 |

(Continued)

OTHER PUBLICATIONS

International Preliminary Report on Patentability issued in International Application No. PCT/US2019/024341, dated Oct. 8, 2020.

(Continued)

*Primary Examiner* — Mohamed G Gabr

(57) ABSTRACT

A surgical applicator for a fastener, the surgical applicator comprising: a handle; a trigger movable relative to the handle between an initial position, an actuated position, and an intermediate position between the initial position and the actuated position; and a lockout mechanism movable relative to the trigger between a locked position and an unlocked position, the lockout mechanism operatively arranged to: lock the trigger in the intermediate position when the trigger is moved from the initial position toward the actuated position; and permit movement of the trigger from the intermediate position toward the initial position or the actuated position when the lockout mechanism is moved from the locked position to the unlocked position.

33 Claims, 16 Drawing Sheets

(51) Int. Cl.
*A61B 17/064* (2006.01)
*A61B 17/068* (2006.01)
(52) U.S. Cl.
CPC ...... *A61B 17/122* (2013.01); *A61B 17/12013* (2013.01); *A61B 2017/1205* (2013.01)
(58) Field of Classification Search
CPC .... A61B 17/12013; A61B 2017/00407; A61B 2017/2936; A61B 2017/2946; A61B 2017/2922; A61B 2017/07214; A61B 17/072; A61B 17/0643; A61B 2017/00243; A61B 17/1285
See application file for complete search history.

(56) References Cited

U.S. PATENT DOCUMENTS

| | | |
|---|---|---|
| 2,659,371 A | 11/1953 | Schnee |
| 3,139,563 A | 6/1964 | Freeman |
| 3,336,133 A | 8/1967 | Makoto |
| 3,361,133 A | 1/1968 | Kimberley |
| 3,525,340 A | 8/1970 | Gilbert |
| 3,746,002 A | 7/1973 | Haller |
| 3,993,076 A | 11/1976 | Fogarty |
| 4,016,883 A | 4/1977 | Wright, Jr. |
| 4,060,089 A | 11/1977 | Noiles |
| 4,241,861 A | 12/1980 | Fleischer |
| 4,257,419 A | 3/1981 | Goeltner |
| 4,271,828 A | 6/1981 | Angelchik |
| 4,390,019 A | 6/1983 | Leveen |
| 4,402,445 A | 9/1983 | Green |
| 4,414,721 A | 11/1983 | Hufnagel |
| 4,487,205 A | 12/1984 | Di Giovanni |
| 4,489,725 A | 12/1984 | Casey |
| 4,506,670 A | 3/1985 | Crossley |
| 4,506,671 A | 3/1985 | Green |
| 4,548,201 A | 10/1985 | Yoon |
| 4,610,250 A | 9/1986 | Green |
| 4,702,247 A | 10/1987 | Blake, III |
| 4,724,839 A | 2/1988 | Bedi |
| 4,754,758 A | 7/1988 | Li |
| 4,805,617 A | 2/1989 | Bedi |
| 4,822,348 A | 4/1989 | Casey |
| 4,924,864 A | 5/1990 | Danzig |
| 4,960,420 A | 10/1990 | Goble |
| 4,976,722 A | 12/1990 | Failla |
| 4,988,355 A | 1/1991 | Leveen |
| 5,002,552 A | 3/1991 | Casey |
| 5,062,846 A | 11/1991 | Oh |
| 5,094,753 A | 3/1992 | Allington |
| 5,127,915 A | 7/1992 | Mattson |
| 5,132,014 A | 7/1992 | Allington |
| 5,156,315 A | 10/1992 | Green |
| 5,156,614 A | 10/1992 | Green |
| 5,160,339 A | 11/1992 | Chen |
| 5,160,624 A | 11/1992 | Clay |
| 5,171,247 A | 12/1992 | Hughett |
| 5,171,249 A | 12/1992 | Stefanchik |
| 5,171,253 A | 12/1992 | Klieman |
| 5,173,188 A | 12/1992 | Winter |
| 5,193,554 A | 3/1993 | McQuilkin |
| 5,198,197 A | 3/1993 | Clay |
| 5,207,691 A | 5/1993 | Nardella |
| 5,246,456 A | 9/1993 | Wilkinson |
| 5,250,195 A | 10/1993 | Winter |
| 5,253,793 A | 10/1993 | Green |
| 5,257,999 A | 11/1993 | Slanetz, Jr. |
| 5,268,102 A | 12/1993 | Clay |
| 5,268,103 A | 12/1993 | Jameson |
| 5,269,930 A | 12/1993 | Jameson |
| 5,282,812 A | 2/1994 | Suarez, Jr. |
| 5,284,488 A | 2/1994 | Sideris |
| 5,296,145 A | 3/1994 | Allington |
| 5,306,234 A | 4/1994 | Johnson |
| 5,314,424 A * | 5/1994 | Nicholas ............ A61B 17/2909 81/319 |
| 5,336,232 A | 8/1994 | Green |
| 5,352,238 A | 10/1994 | Green |
| 5,358,506 A | 10/1994 | Green |
| 5,358,510 A | 10/1994 | Luscombe |
| 5,366,458 A | 11/1994 | Korthoff |
| 5,366,459 A | 11/1994 | Yoon |
| 5,368,600 A | 11/1994 | Failla |
| 5,379,933 A | 1/1995 | Green |
| 5,413,268 A | 5/1995 | Green |
| 5,423,471 A | 6/1995 | Mastri |
| 5,425,705 A | 6/1995 | Evard |
| 5,425,740 A | 6/1995 | Hutchinson, Jr. |
| 5,441,507 A | 8/1995 | Wilk |
| 5,462,215 A | 10/1995 | Viola |
| 5,462,558 A | 10/1995 | Kolesa |
| 5,465,895 A | 11/1995 | Knodel |
| 5,470,006 A | 11/1995 | Rodak |
| 5,470,009 A | 11/1995 | Rodak |
| 5,474,567 A | 12/1995 | Stefanchik |
| 5,485,947 A | 1/1996 | Olson |
| 5,490,856 A | 2/1996 | Person |
| 5,501,693 A | 3/1996 | Gravener |
| 5,507,797 A | 4/1996 | Suzuki |
| 5,509,920 A | 4/1996 | Phillips |
| 5,531,744 A | 7/1996 | Nardella |
| 5,536,251 A | 7/1996 | Evard |
| 5,547,117 A | 8/1996 | Hamblin |
| 5,549,621 A | 8/1996 | Bessler |
| 5,551,622 A | 9/1996 | Yoon |
| 5,554,169 A | 9/1996 | Green |
| 5,560,530 A | 10/1996 | Bolanos |
| 5,569,272 A | 10/1996 | Reed |
| 5,573,169 A | 11/1996 | Green |
| 5,575,802 A | 11/1996 | McQuilkin |
| 5,580,067 A | 12/1996 | Hamblin |
| 5,584,989 A | 12/1996 | Jameson |
| 5,591,178 A | 1/1997 | Green |
| 5,597,107 A | 1/1997 | Knodel |
| 5,601,573 A | 2/1997 | Fogelberg |
| 5,601,707 A | 2/1997 | Clay |
| 5,605,272 A | 2/1997 | Witt |
| 5,605,273 A | 2/1997 | Hamblin |
| 5,614,089 A | 3/1997 | Allington |
| 5,620,452 A | 4/1997 | Yoon |
| 5,624,453 A | 4/1997 | Ahmed |
| 5,626,592 A | 5/1997 | Phillips |
| 5,632,432 A | 5/1997 | Schulze |
| 5,635,070 A | 6/1997 | Allington |
| 5,643,291 A | 7/1997 | Pier |
| 5,643,319 A | 7/1997 | Green |
| 5,645,553 A | 7/1997 | Kolesa |
| 5,653,373 A | 8/1997 | Green |
| 5,653,885 A | 8/1997 | Jameson |
| 5,655,698 A | 8/1997 | Yoon |
| 5,658,300 A | 8/1997 | Bito |
| 5,662,259 A | 9/1997 | Yoon |
| 5,662,260 A | 9/1997 | Yoon |
| 5,665,085 A | 9/1997 | Nardella |
| 5,669,544 A | 9/1997 | Schulze |
| 5,676,676 A | 10/1997 | Porter |
| 5,690,828 A | 11/1997 | Clay |
| 5,695,502 A | 12/1997 | Pier |
| 5,697,938 A | 12/1997 | Jensen |
| 5,706,998 A | 1/1998 | Plyley |
| 5,713,896 A | 2/1998 | Nardella |
| 5,713,912 A | 2/1998 | Porter |
| 5,715,987 A | 2/1998 | Kelley |
| 5,720,756 A | 2/1998 | Green |
| 5,722,982 A | 3/1998 | Ferreira |
| 5,725,537 A | 3/1998 | Green |
| 5,725,538 A | 3/1998 | Green |
| 5,728,110 A | 3/1998 | Vidal |
| 5,735,874 A * | 4/1998 | Measamer ......... A61B 17/2909 606/208 |
| 5,738,498 A | 4/1998 | Allington |
| 5,741,283 A | 4/1998 | Fahy |
| 5,749,893 A | 5/1998 | Vidal |
| 5,750,027 A | 5/1998 | Allington |
| 5,755,559 A | 5/1998 | Allington |

(56) References Cited

U.S. PATENT DOCUMENTS

| | | |
|---|---|---|
| 5,755,726 A | 5/1998 | Pratt |
| 5,759,193 A | 6/1998 | Burbank |
| 5,772,673 A | 6/1998 | Cuny |
| 5,779,718 A | 7/1998 | Green |
| 5,794,834 A | 8/1998 | Hamblin |
| 5,797,932 A | 8/1998 | Min |
| 5,833,695 A | 11/1998 | Yoon |
| 5,833,698 A | 11/1998 | Hinchliffe |
| 5,833,700 A | 11/1998 | Fogelberg |
| 5,843,101 A | 12/1998 | Fry |
| 5,846,255 A | 12/1998 | Casey |
| 5,849,019 A | 12/1998 | Yoon |
| 5,855,311 A | 1/1999 | Hamblin |
| 5,865,791 A | 2/1999 | Whayne |
| 5,868,761 A | 2/1999 | Nicholas |
| 5,868,784 A | 2/1999 | Riza |
| 5,893,879 A | 4/1999 | Hirshowitz |
| 5,911,881 A | 6/1999 | Clay |
| 5,915,615 A | 6/1999 | Bauer |
| 5,921,997 A | 7/1999 | Fogelberg |
| 5,932,095 A | 8/1999 | Walters |
| 5,964,774 A | 10/1999 | McKean |
| 5,972,022 A | 10/1999 | Huxel |
| 5,976,159 A | 11/1999 | Bolduc |
| 6,015,417 A | 1/2000 | Reynolds, Jr. |
| 6,036,706 A | 3/2000 | Morejohn |
| 6,042,599 A | 3/2000 | Huttner |
| 6,051,003 A | 4/2000 | Chu |
| 6,071,408 A | 6/2000 | Allington |
| 6,083,399 A | 7/2000 | Jameson |
| 6,086,767 A | 7/2000 | Walters |
| 6,139,555 A | 10/2000 | Hart |
| 6,139,563 A | 10/2000 | Cosgrove, III |
| 6,149,814 A | 11/2000 | Allington |
| 6,152,144 A | 11/2000 | Lesh |
| 6,162,239 A | 12/2000 | Manhes |
| 6,206,897 B1 | 3/2001 | Jamiolkowski |
| 6,231,561 B1 | 5/2001 | Frazier |
| 6,238,414 B1 | 5/2001 | Griffiths |
| 6,241,890 B1 | 6/2001 | Clay |
| 6,251,267 B1 | 6/2001 | Allington |
| 6,273,897 B1 | 8/2001 | Dalessandro |
| 6,280,407 B1 | 8/2001 | Manna |
| 6,290,674 B1 | 9/2001 | Roue |
| 6,294,088 B1 | 9/2001 | Allington |
| 6,296,769 B1 | 10/2001 | Walters |
| 6,319,410 B1 | 11/2001 | Allington |
| 6,325,810 B1 | 12/2001 | Hamilton |
| 6,328,727 B1 | 12/2001 | Frazier |
| 6,332,864 B1 | 12/2001 | Schweich, Jr. |
| 6,338,710 B1 | 1/2002 | Takahashi |
| 6,379,366 B1 | 4/2002 | Fleischman |
| 6,387,106 B1 | 5/2002 | Howell |
| 6,391,038 B2 | 5/2002 | Vargas |
| 6,406,485 B1 | 6/2002 | Hossain |
| 6,419,669 B1 | 7/2002 | Frazier |
| 6,419,682 B1 | 7/2002 | Appleby |
| 6,421,920 B1 | 7/2002 | Jensen |
| RE37,814 E | 8/2002 | Allgeyer |
| 6,436,097 B1 | 8/2002 | Nardella |
| 6,436,108 B1 | 8/2002 | Mears |
| 6,458,100 B2 | 10/2002 | Roue |
| 6,461,363 B1 | 10/2002 | Gadberry |
| 6,461,368 B2 | 10/2002 | Fogarty |
| 6,478,804 B2 | 11/2002 | Vargas |
| 6,488,689 B1 | 12/2002 | Kaplan |
| 6,503,259 B2 | 1/2003 | Huxel |
| 6,508,829 B1 | 1/2003 | Levinson |
| 6,517,556 B1 | 2/2003 | Monassevitch |
| 6,520,972 B2 | 2/2003 | Peters |
| 6,527,786 B1 | 3/2003 | Davis |
| 6,551,303 B1 | 4/2003 | Van Tassel |
| 6,558,408 B1 | 5/2003 | Fogarty |
| 6,561,969 B2 | 5/2003 | Frazier |
| 6,579,304 B1 | 6/2003 | Hart |
| 6,582,451 B1 | 6/2003 | Marucci |
| 6,592,600 B1 | 7/2003 | Nicolo |
| 6,629,988 B2 | 10/2003 | Weadock |
| 6,638,282 B2 | 10/2003 | Ramsey |
| 6,641,557 B1 | 11/2003 | Frazier |
| 6,644,618 B1 | 11/2003 | Balbo |
| 6,652,555 B1 | 11/2003 | VanTassel |
| 6,652,556 B1 | 11/2003 | VanTassel |
| 6,656,205 B1 | 12/2003 | Manhes |
| 6,663,653 B2 | 12/2003 | Akerfeldt |
| 6,685,715 B2 | 2/2004 | Danitz |
| 6,689,150 B1 | 2/2004 | VanTassel |
| 6,692,507 B2 | 2/2004 | Pugsley |
| 6,699,258 B1 | 3/2004 | Sadler |
| 6,702,825 B2 | 3/2004 | Frazier |
| 6,702,826 B2 | 3/2004 | Liddicoat |
| 6,712,804 B2 | 3/2004 | Roue |
| 6,716,232 B1 | 4/2004 | Vidal |
| 6,723,109 B2 | 4/2004 | Solingen |
| 6,730,108 B2 | 5/2004 | Van Tassel |
| 6,746,461 B2 | 6/2004 | Fry |
| 6,746,472 B2 | 6/2004 | Frazier |
| 6,755,338 B2 | 6/2004 | Hahnen |
| 6,776,783 B1 | 8/2004 | Frantzen |
| 6,776,785 B1 | 8/2004 | Yencho |
| 6,780,195 B2 | 8/2004 | Porat |
| 6,790,172 B2 | 9/2004 | Alferness |
| 6,817,972 B2 | 11/2004 | Snow |
| 6,821,285 B2 | 11/2004 | Laufer |
| 6,830,174 B2 | 12/2004 | Hillstead |
| 6,840,246 B2 | 1/2005 | Downing |
| 6,863,675 B2 | 3/2005 | Wilson, Jr. |
| 6,893,391 B2 | 5/2005 | Taylor |
| 6,916,332 B2 | 7/2005 | Adams |
| 6,926,712 B2 | 8/2005 | Phan |
| 6,949,113 B2 | 9/2005 | Van Tassel |
| 6,974,462 B2 | 12/2005 | Sater |
| 6,994,092 B2 | 2/2006 | Van Der Burg |
| 7,001,412 B2 | 2/2006 | Gallagher |
| 7,033,378 B2 | 4/2006 | Smith |
| 7,044,134 B2 | 5/2006 | Khairkhahan |
| 7,070,083 B2 | 7/2006 | Jankowski |
| 7,077,856 B2 | 7/2006 | Whitman |
| 7,083,636 B2 | 8/2006 | Kortenbach |
| 7,108,703 B2 | 9/2006 | Danitz |
| 7,128,073 B1 | 10/2006 | Van Der Burg |
| 7,152,605 B2 | 12/2006 | Khairkhahan |
| 7,220,272 B2 | 5/2007 | Weadock |
| 7,226,458 B2 | 6/2007 | Kaplan |
| 7,285,131 B1 | 10/2007 | Bombard |
| 7,300,444 B1 | 11/2007 | Nielsen |
| 7,316,696 B2 | 1/2008 | Wilson, Jr. |
| 7,326,223 B2 | 2/2008 | Wilson, Jr. |
| 7,407,076 B2 | 8/2008 | Racenet |
| 7,422,783 B2 | 9/2008 | Tremblay |
| 7,427,279 B2 | 9/2008 | Frazier |
| 7,438,208 B2 | 10/2008 | Larson |
| 7,438,718 B2 | 10/2008 | Milliman |
| 7,473,258 B2 | 1/2009 | Clauson |
| 7,473,261 B2 | 1/2009 | Rennich |
| 7,497,865 B2 | 3/2009 | Willis |
| 7,503,474 B2 | 3/2009 | Hillstead |
| 7,527,634 B2 | 5/2009 | Zenati |
| 7,543,730 B1 | 6/2009 | Marczyk |
| 7,547,315 B2 | 6/2009 | Peterson |
| 7,549,983 B2 | 6/2009 | Roue |
| 7,553,315 B2 | 6/2009 | Kortenbach |
| 7,556,185 B2 | 7/2009 | Viola |
| 7,563,267 B2 | 7/2009 | Goldfarb |
| 7,566,336 B2 | 7/2009 | Corcoran |
| 7,569,064 B1 | 8/2009 | Hausen |
| 7,597,704 B2 | 10/2009 | Frazier |
| 7,628,797 B2 | 12/2009 | Tieu |
| 7,635,073 B2 | 12/2009 | Heinrich |
| 7,645,285 B2 | 1/2010 | Cosgrove |
| 7,648,514 B1 | 1/2010 | Nakao |
| 7,658,311 B2 | 2/2010 | Boudreaux |
| 7,658,312 B2 | 2/2010 | Vidal |
| 7,665,646 B2 | 2/2010 | Prommersberger |

(56) References Cited

U.S. PATENT DOCUMENTS

| | | |
|---|---|---|
| 7,673,782 B2 | 3/2010 | Hess |
| 7,681,772 B2 | 3/2010 | Green |
| 7,686,200 B2 | 3/2010 | Peterson |
| 7,686,759 B2 | 3/2010 | Sater |
| 7,686,820 B2 | 3/2010 | Huitema |
| 7,699,860 B2 | 4/2010 | Huitema |
| 7,713,276 B2 | 5/2010 | Dennis |
| 7,717,312 B2 | 5/2010 | Beetel |
| 7,717,937 B2 | 5/2010 | Wahr |
| 7,722,527 B2 | 5/2010 | Bouchier |
| 7,722,628 B2 | 5/2010 | Stokes |
| 7,722,641 B2 | 5/2010 | Van Der Burg |
| 7,722,643 B2 | 5/2010 | Schaller |
| 7,727,142 B2 | 6/2010 | Hjelle |
| 7,727,189 B2 | 6/2010 | VanTassel |
| 7,731,073 B2 | 6/2010 | Wixey |
| 7,735,493 B2 | 6/2010 | Van Der Burg |
| 7,735,703 B2 | 6/2010 | Morgan |
| 7,740,159 B2 | 6/2010 | Shelton, IV |
| 7,749,249 B2 | 7/2010 | Gelbart |
| 7,753,245 B2 | 7/2010 | Boudreaux |
| 7,753,248 B2 | 7/2010 | Viola |
| 7,757,924 B2 | 7/2010 | Gerbi |
| 7,758,610 B2 | 7/2010 | Kanner |
| 7,766,207 B2 | 8/2010 | Mather |
| 7,766,924 B1 | 8/2010 | Bombard |
| 7,770,774 B2 | 8/2010 | Mastri |
| 7,780,683 B2 | 8/2010 | Roue |
| 7,780,685 B2 | 8/2010 | Hunt |
| 7,794,475 B2 | 9/2010 | Hess |
| 7,819,886 B2 | 10/2010 | Whitfield |
| 7,828,188 B2 | 11/2010 | Jankowski |
| 7,828,810 B2 | 11/2010 | Liddicoat |
| 7,845,533 B2 | 12/2010 | Marczyk |
| 7,845,588 B1 | 12/2010 | Goodick |
| 7,846,168 B2 | 12/2010 | Liddicoat |
| 7,862,571 B2 | 1/2011 | Dennis |
| 7,866,523 B1 | 1/2011 | White |
| 7,891,534 B2 | 2/2011 | Wenchell |
| 7,892,244 B2 | 2/2011 | Monassevitch |
| 7,896,895 B2 | 3/2011 | Boudreaux |
| 7,896,896 B2 | 3/2011 | Viola |
| 7,909,224 B2 | 3/2011 | Prommersberger |
| 7,913,893 B2 | 3/2011 | Mastri |
| 7,926,691 B2 | 4/2011 | Viola |
| 7,931,578 B2 | 4/2011 | Whayne |
| 7,950,561 B2 | 5/2011 | Aranyi |
| 7,951,069 B2 | 5/2011 | Bertolero |
| 7,951,147 B2 | 5/2011 | Privitera |
| 7,954,686 B2 | 6/2011 | Baxter, III |
| 7,959,051 B2 | 6/2011 | Smith |
| 7,959,555 B2 | 6/2011 | Dietz |
| 7,967,178 B2 | 6/2011 | Scirica |
| 7,967,180 B2 | 6/2011 | Scirica |
| 7,992,757 B2 | 8/2011 | Wheeler |
| 8,002,795 B2 | 8/2011 | Beetel |
| 8,007,504 B2 | 8/2011 | Zenati |
| 8,011,553 B2 | 9/2011 | Mastri |
| 8,016,177 B2 | 9/2011 | Bettuchi |
| 8,021,378 B2 | 9/2011 | Sixto, Jr. |
| 8,028,884 B2 | 10/2011 | Sniffin |
| 8,033,439 B2 | 10/2011 | Racenet |
| 8,038,045 B2 | 10/2011 | Bettuchi |
| 8,043,328 B2 | 10/2011 | Hahnen |
| 8,056,787 B2 | 11/2011 | Boudreaux |
| 8,066,168 B2 | 11/2011 | Vidal |
| 8,066,721 B2 | 11/2011 | Kortenbach |
| 8,070,033 B2 | 12/2011 | Milliman |
| 8,070,035 B2 | 12/2011 | Holsten |
| 8,070,038 B2 | 12/2011 | Kostrzewski |
| 8,074,861 B2 | 12/2011 | Ehrenfels |
| 8,074,862 B2 | 12/2011 | Shah |
| 8,080,020 B2 | 12/2011 | Kortenbach |
| 8,080,032 B2 | 12/2011 | Van Der Burg |
| 8,083,118 B2 | 12/2011 | Milliman |
| 8,083,119 B2 | 12/2011 | Prommersberger |
| 8,091,753 B2 | 1/2012 | Viola |
| 8,091,756 B2 | 1/2012 | Viola |
| 8,096,459 B2 | 1/2012 | Ortiz |
| 8,097,015 B2 | 1/2012 | Devellian |
| 8,113,405 B2 | 2/2012 | Milliman |
| 8,113,406 B2 | 2/2012 | Holsten |
| 8,113,407 B2 | 2/2012 | Holsten |
| 8,113,408 B2 | 2/2012 | Wenchell |
| 8,114,123 B2 | 2/2012 | Brenzel |
| 8,118,207 B2 | 2/2012 | Racenet |
| 8,123,101 B2 | 2/2012 | Racenet |
| 8,128,642 B2 | 3/2012 | Heeps |
| 8,152,041 B2 | 4/2012 | Kostrzewski |
| 8,152,823 B2 | 4/2012 | Kassab |
| 8,157,149 B2 | 4/2012 | Olson |
| 8,157,152 B2 | 4/2012 | Holsten |
| 8,162,197 B2 | 4/2012 | Mastri |
| 8,172,122 B2 | 5/2012 | Kasvikis |
| 8,181,837 B2 | 5/2012 | Roy |
| 8,186,558 B2 | 5/2012 | Sapienza |
| 8,187,286 B2 | 5/2012 | Jugenheimer |
| 8,191,752 B2 | 6/2012 | Scirica |
| 8,192,460 B2 | 6/2012 | Orban, III |
| 8,196,796 B2 | 6/2012 | Shelton, IV |
| 8,205,620 B2 | 6/2012 | Taylor |
| 8,205,780 B2 | 6/2012 | Sorrentino |
| 8,205,781 B2 | 6/2012 | Baxter, III |
| 8,210,412 B2 | 7/2012 | Marczyk |
| 8,210,413 B2 | 7/2012 | Whitman |
| 8,210,414 B2 | 7/2012 | Bettuchi |
| 8,210,416 B2 | 7/2012 | Milliman |
| 8,215,532 B2 | 7/2012 | Marczyk |
| 8,220,690 B2 | 7/2012 | Hess |
| 8,221,445 B2 | 7/2012 | Van Tassel |
| 8,225,980 B1 | 7/2012 | Rivera |
| 8,231,040 B2 | 7/2012 | Zemlok |
| 8,235,272 B2 | 8/2012 | Nicholas |
| 8,235,274 B2 | 8/2012 | Cappola |
| 8,236,015 B2 | 8/2012 | Bettuchi |
| 8,240,536 B2 | 8/2012 | Marczyk |
| 8,240,537 B2 | 8/2012 | Marczyk |
| 8,241,322 B2 | 8/2012 | Whitman |
| 8,245,900 B2 | 8/2012 | Scirica |
| 8,245,901 B2 | 8/2012 | Stopek |
| 8,246,634 B2 | 8/2012 | Huitema |
| 8,256,654 B2 | 9/2012 | Bettuchi |
| 8,256,655 B2 | 9/2012 | Sniffin |
| 8,256,656 B2 | 9/2012 | Milliman |
| 8,267,849 B2 | 9/2012 | Wazer |
| 8,272,552 B2 | 9/2012 | Holsten |
| 8,272,553 B2 | 9/2012 | Mastri |
| 8,272,554 B2 | 9/2012 | Whitman |
| 8,276,594 B2 | 10/2012 | Shah |
| 8,276,800 B2 | 10/2012 | Bettuchi |
| 8,276,801 B2 | 10/2012 | Zemlok |
| 8,276,802 B2 | 10/2012 | Kostrzewski |
| 8,281,973 B2 | 10/2012 | Wenchell |
| 8,281,974 B2 | 10/2012 | Hessler |
| 8,281,975 B2 | 10/2012 | Criscuolo |
| 8,286,847 B2 | 10/2012 | Taylor |
| 8,286,848 B2 | 10/2012 | Wenchell |
| 8,287,563 B2 | 10/2012 | Khairkhahan |
| 8,292,146 B2 | 10/2012 | Holsten |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman |
| 8,292,153 B2 | 10/2012 | Jankowski |
| 8,292,154 B2 | 10/2012 | Marczyk |
| 8,292,155 B2 | 10/2012 | Shelton, IV |
| 8,292,156 B2 | 10/2012 | Kostrzewski |
| 8,292,158 B2 | 10/2012 | Sapienza |
| 8,403,197 B2 | 3/2013 | Vidal |
| 8,561,872 B2 | 10/2013 | Wheeler |
| 8,647,350 B2 | 2/2014 | Mohan |
| 8,685,055 B2 | 4/2014 | Vantassel |

(56) References Cited

U.S. PATENT DOCUMENTS

| | | |
|---|---|---|
| 9,072,536 B2 | 7/2015 | Shelton, IV |
| 9,232,941 B2 | 1/2016 | Mandakolathur Vasudevan |
| 9,289,211 B2 | 3/2016 | Williams |
| 9,375,218 B2 | 6/2016 | Wheeler |
| 9,861,359 B2 | 1/2018 | Shelton, IV |
| 10,595,861 B2 | 3/2020 | Wheeler |
| 2001/0005787 A1 | 6/2001 | Oz |
| 2001/0014811 A1 | 8/2001 | Hussein |
| 2001/0016748 A1 | 8/2001 | Tanner |
| 2001/0034536 A1 | 10/2001 | Looper |
| 2001/0039423 A1 | 11/2001 | Skiba |
| 2001/0041914 A1 | 11/2001 | Frazier |
| 2002/0022860 A1 | 2/2002 | Borillo |
| 2002/0022880 A1 | 2/2002 | Melvin |
| 2002/0032454 A1 | 3/2002 | Durgin |
| 2002/0047035 A1 | 4/2002 | Coleman |
| 2002/0049457 A1 | 4/2002 | Kaplan |
| 2002/0055750 A1 | 5/2002 | Durgin |
| 2002/0065535 A1 | 5/2002 | Kneifel |
| 2002/0068945 A1 | 6/2002 | Sixto |
| 2002/0072759 A1 | 6/2002 | Fry |
| 2002/0082621 A1 | 6/2002 | Schurr |
| 2002/0103492 A1 | 8/2002 | Kaplan |
| 2002/0111637 A1 | 8/2002 | Kaplan |
| 2002/0120281 A1 | 8/2002 | Overaker |
| 2002/0138086 A1 | 9/2002 | Sixto |
| 2002/0151889 A1 | 10/2002 | Swanson |
| 2002/0173848 A1 | 11/2002 | Sachs |
| 2002/0177863 A1 | 11/2002 | Mandel |
| 2002/0183770 A1 | 12/2002 | Anderson |
| 2002/0183771 A1 | 12/2002 | Burbank |
| 2002/0183785 A1 | 12/2002 | Howell |
| 2002/0198549 A1 | 12/2002 | Sixto |
| 2003/0023266 A1 | 1/2003 | Borillo |
| 2003/0065340 A1 | 4/2003 | Geitz |
| 2003/0078603 A1 | 4/2003 | Schaller |
| 2003/0114865 A1 | 6/2003 | Sater |
| 2003/0120337 A1 | 6/2003 | Van Tassel |
| 2003/0125729 A1 | 7/2003 | Hooven |
| 2003/0125755 A1 | 7/2003 | Schaller |
| 2003/0130670 A1 | 7/2003 | Anderson |
| 2003/0153930 A1 | 8/2003 | De Canniere |
| 2003/0158464 A1 | 8/2003 | Bertolero |
| 2003/0158604 A1 | 8/2003 | Cauthen |
| 2003/0181929 A1 | 9/2003 | Geitz |
| 2003/0191479 A1 | 10/2003 | Thornton |
| 2003/0191494 A1 | 10/2003 | Gray |
| 2003/0191526 A1 | 10/2003 | Van Tassel |
| 2003/0195531 A1 | 10/2003 | Gardiner |
| 2003/0216757 A1 | 11/2003 | Gerberding |
| 2003/0220660 A1 | 11/2003 | Kortenbach |
| 2003/0220667 A1 | 11/2003 | Van Der Burg |
| 2003/0225421 A1 | 12/2003 | Peavey |
| 2003/0225423 A1 | 12/2003 | Huitema |
| 2003/0225424 A1 | 12/2003 | Benderev |
| 2003/0229367 A1 | 12/2003 | Viola |
| 2003/0233095 A1 | 12/2003 | Urbanski |
| 2003/0236537 A1 | 12/2003 | Hart |
| 2004/0006353 A1 | 1/2004 | Bosley |
| 2004/0024414 A1 | 2/2004 | Downing |
| 2004/0030335 A1 | 2/2004 | Zenati |
| 2004/0034375 A1 | 2/2004 | Ruiz |
| 2004/0049210 A1 | 3/2004 | VanTassel |
| 2004/0059354 A1 | 3/2004 | Smith |
| 2004/0059359 A1 | 3/2004 | Wilson |
| 2004/0073234 A1 | 4/2004 | Chu |
| 2004/0073241 A1 | 4/2004 | Barry |
| 2004/0089312 A1 | 5/2004 | Jordan |
| 2004/0092973 A1 | 5/2004 | Chanduszko |
| 2004/0093024 A1 | 5/2004 | Lousararian |
| 2004/0097980 A1 | 5/2004 | Ferree |
| 2004/0097982 A1 | 5/2004 | Jugenheimer |
| 2004/0111100 A1 | 6/2004 | Benderev |
| 2004/0116948 A1 | 6/2004 | Sixto |
| 2004/0122456 A1 | 6/2004 | Saadat |
| 2004/0122467 A1 | 6/2004 | VanTassel |
| 2004/0127919 A1 | 7/2004 | Trout |
| 2004/0127935 A1 | 7/2004 | VanTassel |
| 2004/0133214 A1 | 7/2004 | Kayan |
| 2004/0133215 A1 | 7/2004 | Baxter |
| 2004/0133219 A1 | 7/2004 | Forsell |
| 2004/0138683 A1 | 7/2004 | Shelton |
| 2004/0186486 A1 | 9/2004 | Roue |
| 2004/0193188 A1 | 9/2004 | Francese |
| 2004/0199178 A1 | 10/2004 | Small |
| 2004/0230222 A1 | 11/2004 | Van Der Burg |
| 2004/0260314 A1* | 12/2004 | Lizardi .............. A61B 17/0469 606/144 |
| 2005/0004652 A1 | 1/2005 | Van Der Burg |
| 2005/0021061 A1 | 1/2005 | Dennis |
| 2005/0021062 A1 | 1/2005 | Dennis |
| 2005/0027308 A1 | 2/2005 | Davis |
| 2005/0049573 A1 | 3/2005 | Van Tassel |
| 2005/0059988 A1 | 3/2005 | Danitz |
| 2005/0125010 A1 | 6/2005 | Smith |
| 2005/0139635 A1 | 6/2005 | Wukusick |
| 2005/0143767 A1 | 6/2005 | Kimura |
| 2005/0146069 A1 | 7/2005 | Kanan |
| 2005/0149068 A1 | 7/2005 | Williams |
| 2005/0149069 A1 | 7/2005 | Bertolero |
| 2005/0149988 A1 | 7/2005 | Grannan |
| 2005/0149989 A1 | 7/2005 | Lupoi |
| 2005/0154404 A1 | 7/2005 | Liddicoat |
| 2005/0165421 A1 | 7/2005 | Wilson, Jr. |
| 2005/0165422 A1 | 7/2005 | Wilson, Jr. |
| 2005/0165423 A1 | 7/2005 | Gallagher |
| 2005/0165424 A1 | 7/2005 | Gallagher |
| 2005/0171560 A1 | 8/2005 | Hughett |
| 2005/0177180 A1 | 8/2005 | Kaganov |
| 2005/0177182 A1 | 8/2005 | Van Der Burg |
| 2005/0177224 A1 | 8/2005 | Fogarty |
| 2005/0177232 A1 | 8/2005 | Ashton |
| 2005/0187569 A1 | 8/2005 | Dahl |
| 2005/0234543 A1 | 10/2005 | Glaser |
| 2005/0251184 A1 | 11/2005 | Anderson |
| 2005/0273122 A1 | 12/2005 | Theroux |
| 2005/0277955 A1 | 12/2005 | Palmer |
| 2005/0277959 A1 | 12/2005 | Cosgrove |
| 2006/0004388 A1 | 1/2006 | Whayne |
| 2006/0004390 A1 | 1/2006 | Rosenberg |
| 2006/0020162 A1 | 1/2006 | Whayne |
| 2006/0020271 A1 | 1/2006 | Stewart |
| 2006/0020275 A1 | 1/2006 | Goldfarb |
| 2006/0025812 A1 | 2/2006 | Shelton, IV |
| 2006/0100644 A1 | 5/2006 | Viola |
| 2006/0100649 A1 | 5/2006 | Hart |
| 2006/0111735 A1 | 5/2006 | Crainich |
| 2006/0151567 A1 | 7/2006 | Roy |
| 2006/0217749 A1 | 9/2006 | Wilson, Jr. |
| 2006/0264979 A1 | 11/2006 | Shepard |
| 2006/0264987 A1 | 11/2006 | Sgro |
| 2007/0005108 A1 | 1/2007 | Simhon |
| 2007/0016228 A1 | 1/2007 | Salas |
| 2007/0060951 A1 | 3/2007 | Shannon |
| 2007/0073274 A1 | 3/2007 | Chin |
| 2007/0083218 A1 | 4/2007 | Morris |
| 2007/0083227 A1 | 4/2007 | Van Der Burg |
| 2007/0106314 A1 | 5/2007 | Dunn |
| 2007/0112365 A1 | 5/2007 | Hilal |
| 2007/0118161 A1 | 5/2007 | Kennedy |
| 2007/0118163 A1 | 5/2007 | Boudreaux |
| 2007/0135826 A1 | 6/2007 | Zaver |
| 2007/0149988 A1 | 6/2007 | Michler |
| 2007/0149989 A1 | 6/2007 | Santilli |
| 2007/0149995 A1 | 6/2007 | Quinn |
| 2007/0162060 A1 | 7/2007 | Wild |
| 2007/0167964 A1 | 7/2007 | Willis |
| 2007/0179512 A1 | 8/2007 | Olsen |
| 2007/0185506 A1 | 8/2007 | Jackson |
| 2007/0191868 A1 | 8/2007 | Theroux |
| 2007/0203391 A1 | 8/2007 | Bloom |
| 2007/0208357 A1 | 9/2007 | Houser |
| 2007/0213747 A1 | 9/2007 | Monassevitch |
| 2007/0246505 A1 | 10/2007 | Pace-Floridia |

(56) References Cited

U.S. PATENT DOCUMENTS

| | | |
|---|---|---|
| 2007/0250086 A1 | 10/2007 | Wiley |
| 2007/0260278 A1 | 11/2007 | Wheeler |
| 2007/0265640 A1 | 11/2007 | Kortenbach |
| 2007/0265641 A1 | 11/2007 | Roue |
| 2007/0265642 A1 | 11/2007 | Chanduszko |
| 2007/0270891 A1 | 11/2007 | McGuckin, Jr. |
| 2007/0276417 A1 | 11/2007 | Mendes, Jr. |
| 2007/0299469 A1* | 12/2007 | Carpenter .......... A61B 17/2909 606/205 |
| 2008/0009866 A1 | 1/2008 | Alamin |
| 2008/0021466 A1 | 1/2008 | Shadduck |
| 2008/0021484 A1 | 1/2008 | Catanese, III |
| 2008/0027471 A1 | 1/2008 | Hauri |
| 2008/0027478 A1 | 1/2008 | Connors |
| 2008/0033241 A1 | 2/2008 | Peh |
| 2008/0033457 A1 | 2/2008 | Francischelli |
| 2008/0039879 A1 | 2/2008 | Chin |
| 2008/0039922 A1 | 2/2008 | Miles |
| 2008/0060658 A1 | 3/2008 | Doorschodt |
| 2008/0071294 A1 | 3/2008 | Bender |
| 2008/0078800 A1 | 4/2008 | Hess |
| 2008/0078802 A1 | 4/2008 | Hess |
| 2008/0078803 A1 | 4/2008 | Shelton |
| 2008/0078804 A1 | 4/2008 | Shelton |
| 2008/0078806 A1 | 4/2008 | Omaits |
| 2008/0078808 A1 | 4/2008 | Hess |
| 2008/0097571 A1 | 4/2008 | Denison |
| 2008/0105265 A1 | 5/2008 | Pannell |
| 2008/0125795 A1 | 5/2008 | Kaplan |
| 2008/0125796 A1 | 5/2008 | Graham |
| 2008/0132891 A1 | 6/2008 | Nobis |
| 2008/0140095 A1 | 6/2008 | Smith |
| 2008/0147083 A1 | 6/2008 | Vold |
| 2008/0177292 A1 | 7/2008 | Jacobs |
| 2008/0183283 A1 | 7/2008 | Downing |
| 2008/0208324 A1 | 8/2008 | Glithero |
| 2008/0215090 A1 | 9/2008 | Gonzales |
| 2008/0234785 A1 | 9/2008 | Nakayama |
| 2008/0249547 A1 | 10/2008 | Dunn |
| 2008/0269787 A1 | 10/2008 | Laufer |
| 2008/0287989 A1 | 11/2008 | Weisel |
| 2008/0294179 A1 | 11/2008 | Balbierz |
| 2008/0300686 A1 | 12/2008 | Khoo |
| 2008/0312670 A1 | 12/2008 | Lutze |
| 2008/0314956 A1 | 12/2008 | Boudreaux |
| 2008/0314961 A1 | 12/2008 | Boudreaux |
| 2008/0319456 A1 | 12/2008 | Hart |
| 2009/0001121 A1 | 1/2009 | Hess |
| 2009/0001124 A1 | 1/2009 | Hess |
| 2009/0005808 A1 | 1/2009 | Hess |
| 2009/0012545 A1 | 1/2009 | Williamson, IV |
| 2009/0020584 A1 | 1/2009 | Soltz |
| 2009/0048665 A1 | 2/2009 | Miron |
| 2009/0054916 A1 | 2/2009 | Meier |
| 2009/0088783 A1 | 4/2009 | Kennedy |
| 2009/0093826 A1 | 4/2009 | Warder-Gabaldon |
| 2009/0105731 A1 | 4/2009 | Priewe |
| 2009/0112249 A1 | 4/2009 | Miles |
| 2009/0118748 A1 | 5/2009 | Pugsley |
| 2009/0131959 A1 | 5/2009 | Rolland |
| 2009/0138028 A1 | 5/2009 | Wells |
| 2009/0163937 A1 | 6/2009 | Kassab |
| 2009/0171380 A1 | 7/2009 | Whiting |
| 2009/0171386 A1 | 7/2009 | Amplatz |
| 2009/0177212 A1 | 7/2009 | Carley |
| 2009/0182326 A1 | 7/2009 | Zenati |
| 2009/0182374 A1 | 7/2009 | Keith |
| 2009/0182419 A1 | 7/2009 | Bolling |
| 2009/0187198 A1 | 7/2009 | Weitzner |
| 2009/0206127 A1 | 8/2009 | Danielson |
| 2009/0209986 A1 | 8/2009 | Stewart |
| 2009/0222025 A1 | 9/2009 | Joseph, III |
| 2009/0240267 A1 | 9/2009 | Crawley |
| 2009/0240268 A1 | 9/2009 | Kassab |
| 2009/0264880 A1 | 10/2009 | Solem |
| 2009/0277948 A1 | 11/2009 | Beardsley |
| 2010/0023023 A1 | 1/2010 | Popovic |
| 2010/0063541 A1 | 3/2010 | Brunelle |
| 2010/0069924 A1 | 3/2010 | Kochman |
| 2010/0069928 A1 | 3/2010 | Bauer |
| 2010/0069930 A1 | 3/2010 | Roslin |
| 2010/0082047 A1 | 4/2010 | Cosgrove |
| 2010/0114124 A1 | 5/2010 | Kelleher |
| 2010/0114133 A1 | 5/2010 | Huitema |
| 2010/0114134 A1 | 5/2010 | Mcintyre |
| 2010/0114157 A1 | 5/2010 | Sabanathan |
| 2010/0115739 A1 | 5/2010 | Mathur |
| 2010/0121359 A1 | 5/2010 | Atui |
| 2010/0125288 A1 | 5/2010 | Gelfand |
| 2010/0130965 A1 | 5/2010 | Sibbitt, Jr. |
| 2010/0137885 A1 | 6/2010 | Ortiz |
| 2010/0145361 A1 | 6/2010 | Francischelli |
| 2010/0155453 A1 | 6/2010 | Bombard |
| 2010/0163054 A1 | 7/2010 | Breznel |
| 2010/0168791 A1 | 7/2010 | Kassab |
| 2010/0179570 A1 | 7/2010 | Privitera |
| 2010/0185219 A1 | 7/2010 | Gertzman |
| 2010/0185221 A1 | 7/2010 | Shipp |
| 2010/0186750 A1 | 7/2010 | Tran |
| 2010/0191257 A1 | 7/2010 | Boulnois |
| 2010/0191279 A1 | 7/2010 | Kassab |
| 2010/0204716 A1 | 8/2010 | Stewart |
| 2010/0211046 A1 | 8/2010 | Adams |
| 2010/0217314 A1 | 8/2010 | Holsten |
| 2010/0222789 A1 | 9/2010 | Gelbart |
| 2010/0228269 A1 | 9/2010 | Garrison |
| 2010/0228279 A1 | 9/2010 | Miles |
| 2010/0228285 A1 | 9/2010 | Miles |
| 2010/0234862 A1 | 9/2010 | Patel |
| 2010/0241139 A1 | 9/2010 | Harshman |
| 2010/0256660 A1 | 10/2010 | Anderson |
| 2010/0286718 A1 | 11/2010 | Kassab |
| 2010/0292713 A1* | 11/2010 | Cohn ................ A61B 17/0682 606/143 |
| 2010/0292719 A1 | 11/2010 | Ducharme |
| 2010/0324572 A1 | 12/2010 | Needleman |
| 2010/0324585 A1 | 12/2010 | Miles |
| 2010/0324586 A1 | 12/2010 | Miles |
| 2010/0324587 A1 | 12/2010 | Miles |
| 2010/0324588 A1 | 12/2010 | Miles |
| 2010/0331862 A1 | 12/2010 | Monassevitch |
| 2010/0331880 A1 | 12/2010 | Stopek |
| 2011/0009853 A1 | 1/2011 | Bertolero |
| 2011/0022079 A1 | 1/2011 | Miles |
| 2011/0036896 A1 | 2/2011 | Buesseler |
| 2011/0046437 A1 | 2/2011 | Kassab |
| 2011/0046641 A1 | 2/2011 | Kassab |
| 2011/0054515 A1 | 3/2011 | Bridgeman |
| 2011/0068143 A1 | 3/2011 | Laufer |
| 2011/0071547 A1 | 3/2011 | Mcbrayer |
| 2011/0071555 A1 | 3/2011 | Mcbrayer |
| 2011/0082495 A1 | 4/2011 | Ruiz |
| 2011/0112559 A1 | 5/2011 | Monassevitch |
| 2011/0125171 A1 | 5/2011 | Viola |
| 2011/0144661 A1 | 6/2011 | Houser |
| 2011/0152895 A1 | 6/2011 | Nyuli |
| 2011/0155788 A1 | 6/2011 | Hillstead |
| 2011/0174863 A1 | 7/2011 | Shelton, IV |
| 2011/0178534 A1 | 7/2011 | Whitman |
| 2011/0178535 A1 | 7/2011 | Whitman |
| 2011/0178539 A1 | 7/2011 | Holmes, Jr. |
| 2011/0190791 A1 | 8/2011 | Jacobs |
| 2011/0190809 A1 | 8/2011 | Mohan |
| 2011/0208233 A1 | 8/2011 | Mcguckin, Jr. |
| 2011/0218566 A1 | 9/2011 | Van Der Burg |
| 2011/0224700 A1 | 9/2011 | Schmidt |
| 2011/0224701 A1 | 9/2011 | Menn |
| 2011/0230903 A1 | 9/2011 | Bertolero |
| 2011/0238094 A1 | 9/2011 | Thomas |
| 2011/0245849 A1 | 10/2011 | Jabba |
| 2011/0270285 A1 | 11/2011 | Lissa |
| 2011/0270303 A1 | 11/2011 | Wheeler |
| 2011/0295290 A1 | 12/2011 | Whitfield |
| 2011/0295291 A1 | 12/2011 | Trivisani |

(56) References Cited

U.S. PATENT DOCUMENTS

| | | |
|---|---|---|
| 2011/0313437 A1 | 12/2011 | Yeh |
| 2012/0010635 A1 | 1/2012 | Yeretsian |
| 2012/0035631 A1 | 2/2012 | Hughett, Sr. |
| 2012/0035643 A1 | 2/2012 | Khairkhahan |
| 2012/0059400 A1 | 3/2012 | Williamson, IV |
| 2012/0065662 A1 | 3/2012 | Van Der Burg |
| 2012/0065667 A1 | 3/2012 | Javois |
| 2012/0071918 A1 | 3/2012 | Amin |
| 2012/0074198 A1 | 3/2012 | Huitema |
| 2012/0080478 A1 | 4/2012 | Morgan |
| 2012/0080479 A1 | 4/2012 | Shelton, IV |
| 2012/0080480 A1 | 4/2012 | Woodard, Jr. |
| 2012/0080481 A1 | 4/2012 | Widenhouse |
| 2012/0080482 A1 | 4/2012 | Schall |
| 2012/0080483 A1 | 4/2012 | Riestenberg |
| 2012/0080484 A1 | 4/2012 | Morgan |
| 2012/0080485 A1 | 4/2012 | Woodard, Jr. |
| 2012/0080486 A1 | 4/2012 | Woodard, Jr. |
| 2012/0080487 A1 | 4/2012 | Woodard, Jr. |
| 2012/0080488 A1 | 4/2012 | Shelton, IV |
| 2012/0080489 A1 | 4/2012 | Shelton, IV |
| 2012/0080490 A1 | 4/2012 | Shelton, IV |
| 2012/0080491 A1 | 4/2012 | Shelton, IV |
| 2012/0080503 A1 | 4/2012 | Woodard, Jr. |
| 2012/0083803 A1 | 4/2012 | Patel |
| 2012/0093903 A1 | 4/2012 | Roth |
| 2012/0101509 A1 | 4/2012 | Paganon |
| 2012/0109161 A1 | 5/2012 | Privitera |
| 2012/0111920 A1 | 5/2012 | Kostrzewski |
| 2012/0123445 A1 | 5/2012 | Hughett, Sr. |
| 2012/0130402 A1 | 5/2012 | Heeps |
| 2012/0130421 A1 | 5/2012 | Hafez |
| 2012/0145767 A1 | 6/2012 | Shah |
| 2012/0145768 A1 | 6/2012 | Sorrentino |
| 2012/0158022 A1 | 6/2012 | Kaplan |
| 2012/0160890 A1 | 6/2012 | Holcomb |
| 2012/0172927 A1 | 7/2012 | Campbell |
| 2012/0209297 A1 | 8/2012 | Jugenheimer |
| 2012/0228359 A1 | 9/2012 | Viola |
| 2012/0239083 A1 | 9/2012 | Kreidler |
| 2012/0241503 A1 | 9/2012 | Baxter, III |
| 2012/0241505 A1 | 9/2012 | Alexander, III |
| 2012/0245605 A1 | 9/2012 | Nicholson, IV |
| 2012/0248169 A1 | 10/2012 | Widenhouse |
| 2012/0271337 A1 | 10/2012 | Figulla |
| 2012/0283585 A1 | 11/2012 | Werneth |
| 2012/0283773 A1 | 11/2012 | Van Tassel |
| 2013/0023911 A1* | 1/2013 | Esanu .................. A61B 17/29<br>606/158 |
| 2014/0163605 A1 | 6/2014 | Vantassel |
| 2015/0129634 A1* | 5/2015 | Shelton, IV ..... A61B 17/07292<br>227/176.1 |
| 2015/0164524 A1 | 6/2015 | Malkowski |
| 2015/0223807 A1* | 8/2015 | Mohan ............... A61B 17/0643<br>227/178.1 |
| 2016/0270784 A1 | 9/2016 | Wheeler |
| 2016/0296233 A1 | 10/2016 | Wheeler |

FOREIGN PATENT DOCUMENTS

| | | |
|---|---|---|
| DE | 19520158 A1 | 12/1996 |
| DE | 19534320 C1 | 2/1997 |
| DE | 19537299 A1 | 4/1997 |
| DE | 19707382 A1 | 9/1997 |
| DE | 29716753 U1 | 10/1997 |
| DE | 29715758 U1 | 1/1998 |
| DE | 29822558 U1 | 2/1999 |
| DE | 19738306 A1 | 3/1999 |
| DE | 19741053 A1 | 4/1999 |
| DE | 29913246 U1 | 9/1999 |
| DE | 19925304 A1 | 12/1999 |
| DE | 19832739 A1 | 2/2000 |
| DE | 19860685 A1 | 7/2000 |
| DE | 19858577 C1 | 9/2000 |
| DE | 19951940 A1 | 6/2001 |
| DE | 10212385 A1 | 11/2002 |
| DE | 20214068 U1 | 11/2002 |
| DE | 20208744 U1 | 1/2003 |
| DE | 10203946 A1 | 3/2003 |
| DE | 10347391 A1 | 5/2005 |
| DE | 102004015223 A1 | 10/2005 |
| DE | 102004026617 A1 | 12/2005 |
| DE | 202007003398 U1 | 6/2007 |
| DE | 102009018819 A1 | 10/2010 |
| DE | 102009018821 A1 | 10/2010 |
| DE | 202010008941 U1 | 12/2010 |
| DE | 202012001672 U1 | 3/2012 |
| DE | 102010060322 A1 | 5/2012 |
| EP | 138687 A1 | 4/1985 |
| EP | 0169044 A2 | 1/1986 |
| EP | 0314064 A2 | 5/1989 |
| EP | 324549 A2 | 7/1989 |
| EP | 476523 A2 | 3/1992 |
| EP | 489436 A1 | 6/1992 |
| EP | 0490411 | 6/1992 |
| EP | 492283 A1 | 7/1992 |
| EP | 0510826 | 10/1992 |
| EP | 537572 A2 | 4/1993 |
| EP | 567965 A2 | 11/1993 |
| EP | 576835 A2 | 1/1994 |
| EP | 578425 A1 | 1/1994 |
| EP | 0594002 A1 | 4/1994 |
| EP | 0594004 A1 | 4/1994 |
| EP | 598976 A2 | 6/1994 |
| EP | 0600182 A2 | 6/1994 |
| EP | 0609612 | 8/1994 |
| EP | 0610307 A1 | 8/1994 |
| EP | 674876 A2 | 10/1995 |
| EP | 676173 A1 | 10/1995 |
| EP | 0681810 | 11/1995 |
| EP | 696179 A1 | 2/1996 |
| EP | 699415 A2 | 3/1996 |
| EP | 0704190 A1 | 4/1996 |
| EP | 714633 A1 | 6/1996 |
| EP | 0724405 | 8/1996 |
| EP | 754433 A2 | 1/1997 |
| EP | 758214 A1 | 2/1997 |
| EP | 763346 A1 | 3/1997 |
| EP | 763347 A1 | 3/1997 |
| EP | 0780107 | 6/1997 |
| EP | 0790804 | 8/1997 |
| EP | 793944 A1 | 9/1997 |
| EP | 885595 A1 | 12/1998 |
| EP | 0893970 | 2/1999 |
| EP | 897696 A1 | 2/1999 |
| EP | 0910293 | 4/1999 |
| EP | 981296 A1 | 3/2000 |
| EP | 1064883 A1 | 1/2001 |
| EP | 1072225 A2 | 1/2001 |
| EP | 1090592 A1 | 4/2001 |
| EP | 1100382 A1 | 5/2001 |
| EP | 1199990 A1 | 5/2002 |
| EP | 1233708 A2 | 8/2002 |
| EP | 1250096 A2 | 10/2002 |
| EP | 1254636 A2 | 11/2002 |
| EP | 1256317 A2 | 11/2002 |
| EP | 1289428 A2 | 3/2003 |
| EP | 1289432 A1 | 3/2003 |
| EP | 1326544 A1 | 7/2003 |
| EP | 1339327 A2 | 9/2003 |
| EP | 1342451 A1 | 9/2003 |
| EP | 1357843 B1 | 11/2003 |
| EP | 1389065 B1 | 2/2004 |
| EP | 1399072 B1 | 3/2004 |
| EP | 1417933 | 5/2004 |
| EP | 1418848 B1 | 5/2004 |
| EP | 1437972 B1 | 7/2004 |
| EP | 1455653 B1 | 9/2004 |
| EP | 1462061 A2 | 9/2004 |
| EP | 1462062 A2 | 9/2004 |
| EP | 1465532 B1 | 10/2004 |
| EP | 1492460 B1 | 1/2005 |
| EP | 1545332 B1 | 6/2005 |

(56) References Cited

FOREIGN PATENT DOCUMENTS

| | | |
|---|---|---|
| EP | 1545333 B1 | 6/2005 |
| EP | 1600108 A2 | 11/2005 |
| EP | 1603465 B1 | 12/2005 |
| EP | 1684641 B1 | 8/2006 |
| EP | 1694218 A2 | 8/2006 |
| EP | 1709915 A1 | 10/2006 |
| EP | 1723914 A1 | 11/2006 |
| EP | 1757235 A1 | 2/2007 |
| EP | 1767157 A1 | 3/2007 |
| EP | 1774914 A1 | 4/2007 |
| EP | 1774915 A1 | 4/2007 |
| EP | 1810622 A1 | 7/2007 |
| EP | 1813214 A1 | 8/2007 |
| EP | 1815803 A1 | 8/2007 |
| EP | 1829489 A1 | 9/2007 |
| EP | 1852141 A2 | 11/2007 |
| EP | 1874196 B1 | 1/2008 |
| EP | 1908412 A2 | 4/2008 |
| EP | 1908413 A1 | 4/2008 |
| EP | 1908415 A1 | 4/2008 |
| EP | 1913881 A1 | 4/2008 |
| EP | 1949863 A1 | 7/2008 |
| EP | 1971276 B1 | 9/2008 |
| EP | 1980214 A2 | 10/2008 |
| EP | 1983906 B1 | 10/2008 |
| EP | 1993451 B1 | 11/2008 |
| EP | 2010066 B1 | 1/2009 |
| EP | 2019633 B1 | 2/2009 |
| EP | 2044892 A2 | 4/2009 |
| EP | 2074954 A1 | 7/2009 |
| EP | 2098170 A2 | 9/2009 |
| EP | 2098175 A1 | 9/2009 |
| EP | 2110082 A1 | 10/2009 |
| EP | 2110083 A2 | 10/2009 |
| EP | 2110084 A2 | 10/2009 |
| EP | 2113209 A1 | 11/2009 |
| EP | 2116193 A1 | 11/2009 |
| EP | 2116194 A2 | 11/2009 |
| EP | 2116195 A1 | 11/2009 |
| EP | 2130501 A1 | 12/2009 |
| EP | 2151204 A1 | 2/2010 |
| EP | 2158854 A1 | 3/2010 |
| EP | 2241265 A1 | 10/2010 |
| EP | 2253279 A1 | 11/2010 |
| EP | 2286737 A1 | 2/2011 |
| EP | 2316351 A2 | 5/2011 |
| EP | 2328482 A1 | 6/2011 |
| EP | 2347722 A1 | 7/2011 |
| EP | 2380509 A2 | 10/2011 |
| EP | 2389878 A1 | 11/2011 |
| EP | 2392268 A1 | 12/2011 |
| EP | 2409654 A2 | 1/2012 |
| EP | 2412318 A2 | 2/2012 |
| EP | 2417916 A2 | 2/2012 |
| EP | 2446838 A2 | 5/2012 |
| EP | 2455007 A2 | 5/2012 |
| EP | 2455012 A2 | 5/2012 |
| EP | 2462880 A2 | 6/2012 |
| EP | 2497431 A1 | 9/2012 |
| EP | 2520228 A2 | 11/2012 |
| EP | 3120781 | 1/2017 |
| FR | 2598905 A1 | 11/1987 |
| FR | 2815842 A1 | 5/2002 |
| GB | 1530282 A | 10/1978 |
| GB | 2150440 A | 7/1985 |
| GB | 2177748 A | 1/1987 |
| GB | 2190297 A | 11/1987 |
| GB | 2226958 A | 7/1990 |
| GB | 2443736 A | 5/2008 |
| JP | S58190432 | 11/1983 |
| JP | S60501392 | 8/1985 |
| JP | S62246357 | 10/1987 |
| JP | 3336540 | 10/1993 |
| JP | H08336540 | 12/1996 |
| JP | 2006507042 A | 3/2006 |
| JP | 2007535997 | 12/2007 |
| JP | 2009536082 A | 10/2009 |
| RU | 2093201 C1 | 10/1996 |
| RU | 2110221 C1 | 5/1998 |
| RU | 2196530 C1 | 1/2003 |
| RU | 2245113 C2 | 1/2005 |
| RU | 2261057 C1 | 9/2005 |
| RU | 2299023 C2 | 1/2007 |
| RU | 2008141508 | 5/2010 |
| WO | 1993009717 A1 | 5/1993 |
| WO | 9415535 | 7/1994 |
| WO | 1996002279 A2 | 2/1996 |
| WO | 1996019146 A1 | 6/1996 |
| WO | 9846301 | 10/1998 |
| WO | 9913780 A1 | 3/1999 |
| WO | 9920183 | 4/1999 |
| WO | 1999018858 A1 | 4/1999 |
| WO | 2000032113 A1 | 6/2000 |
| WO | 2000054662 A1 | 9/2000 |
| WO | 0110306 | 2/2001 |
| WO | 2001028432 A1 | 4/2001 |
| WO | 2001043649 A1 | 6/2001 |
| WO | 0224080 A2 | 3/2002 |
| WO | 2002017809 A1 | 3/2002 |
| WO | 2002082975 A2 | 10/2002 |
| WO | 2002087425 A2 | 11/2002 |
| WO | 2003011150 A1 | 2/2003 |
| WO | 2003022159 A1 | 3/2003 |
| WO | 2003037162 A2 | 5/2003 |
| WO | 2003041596 A1 | 5/2003 |
| WO | 2003053256 A1 | 7/2003 |
| WO | 2003082076 A2 | 10/2003 |
| WO | 2003082129 A2 | 10/2003 |
| WO | 2003086206 A1 | 10/2003 |
| WO | 03090633 A2 | 11/2003 |
| WO | 2003096881 A2 | 11/2003 |
| WO | 2004004542 A2 | 1/2004 |
| WO | 2004023976 A2 | 3/2004 |
| WO | 2004026148 A1 | 4/2004 |
| WO | 2004026201 A1 | 4/2004 |
| WO | 2004026350 A2 | 4/2004 |
| WO | 2004032761 A1 | 4/2004 |
| WO | 2004045370 A2 | 6/2004 |
| WO | 2004058079 A2 | 7/2004 |
| WO | 2004066846 A1 | 8/2004 |
| WO | 2004110285 A1 | 12/2004 |
| WO | 2005027721 A2 | 3/2005 |
| WO | 2005046453 A2 | 5/2005 |
| WO | 2005046453 A3 | 5/2005 |
| WO | 2005060838 A2 | 7/2005 |
| WO | 2005060838 A3 | 7/2005 |
| WO | 2005063133 A1 | 7/2005 |
| WO | 2005072105 A2 | 8/2005 |
| WO | 2005086824 A2 | 9/2005 |
| WO | 2005096960 A1 | 10/2005 |
| WO | 2005120326 A2 | 12/2005 |
| WO | 2006009545 A1 | 1/2006 |
| WO | 2006042110 A2 | 4/2006 |
| WO | 2006085389 A1 | 8/2006 |
| WO | 2006102578 A1 | 9/2006 |
| WO | 2006126979 A2 | 11/2006 |
| WO | 2007009099 A2 | 1/2007 |
| WO | 2007016288 A2 | 2/2007 |
| WO | 2007019268 A2 | 2/2007 |
| WO | 2007019321 A2 | 2/2007 |
| WO | 2007025014 A2 | 3/2007 |
| WO | 2006126979 A3 | 5/2007 |
| WO | 2007090291 A1 | 8/2007 |
| WO | 2007106342 A2 | 9/2007 |
| WO | 2007131110 A2 | 11/2007 |
| WO | 2008020975 A2 | 2/2008 |
| WO | 2008024671 A2 | 2/2008 |
| WO | 2008024672 A2 | 2/2008 |
| WO | 2008033558 A2 | 3/2008 |
| WO | 2008070763 A1 | 6/2008 |
| WO | 2008137833 A2 | 11/2008 |
| WO | 2009005527 A1 | 1/2009 |
| WO | 2009094078 A2 | 7/2009 |
| WO | 2009108464 A1 | 9/2009 |

(56) References Cited

FOREIGN PATENT DOCUMENTS

| | | |
|---|---|---|
| WO | 2009129369 A1 | 10/2009 |
| WO | 2009135022 A1 | 11/2009 |
| WO | 2009136397 A2 | 11/2009 |
| WO | 2010006028 A1 | 1/2010 |
| WO | 2010011661 A1 | 1/2010 |
| WO | 2010055232 A1 | 5/2010 |
| WO | 2010080386 A2 | 7/2010 |
| WO | 2010091913 A1 | 8/2010 |
| WO | 2011019848 A1 | 2/2011 |
| WO | 2011025877 A1 | 3/2011 |
| WO | 2011028196 A2 | 3/2011 |
| WO | 2011050658 A1 | 5/2011 |
| WO | 2011057282 A2 | 5/2011 |
| WO | 2011060386 A2 | 5/2011 |
| WO | 2011066533 A1 | 6/2011 |
| WO | 2011078959 A1 | 6/2011 |
| WO | 2011081791 A1 | 7/2011 |
| WO | 2011083027 A1 | 7/2011 |
| WO | 2011091185 A1 | 7/2011 |
| WO | 2011112577 A1 | 9/2011 |
| WO | 2012021082 A2 | 2/2012 |
| WO | 2012021207 A1 | 2/2012 |
| WO | 2012048387 A1 | 4/2012 |
| WO | 2012064643 A1 | 5/2012 |
| WO | 2012125621 A1 | 9/2012 |
| WO | 2012129317 A2 | 9/2012 |

OTHER PUBLICATIONS

International Search Report and Written Opinion of PCT Application No. PCT/US07/068147, dated Sep. 17, 2008, 6 pages total.
Amendment dated Jul. 22, 2011 for U.S. Appl. No. 13/117,863.
Office action dated Dec. 7, 2010 for U.S. Appl. No. 11/744,135.
Response to final office action dated Aug. 1, 2012 for U.S. Appl. No. 11/155,305.
Response to office action dated Apr. 28, 2009 for U.S. Appl. No. 11/155,305.
Revised Brief on Appeal dated Sep. 7, 2010 for U.S. Appl. No. 11/003,696 (14 pages).
International Search Report and Written Opinion of PCT Patent Application No. PCT/US2010/045216, dated Oct. 12, 2010, 8 pages total.
Office action dated Jan. 31, 2013 for U.S. Appl. No. 12/849,534.
Office action dated Feb. 24, 2012 for U.S. Appl. No. 13/180,373.
Supplemental EP Search Report dated Feb. 3, 2014 for EP Patent Application No. 07761828.8, 5 pages.
Burke, Redmond P., et al., "Improved Surgical Approach to Left Atrial Appendage Aneurysm", Journal of Cardiac Surgery, 1992, vol. 7, No. 2, pp. 104-107.
Johnson, W. Dudley, et al., "The left atrial appendage: our most lethal human attachment! Surgical implications", European Journal of Cardio-thoracic Surgery, 2000, vol. 17, pp. 718-722.
Cox, James L., "The surgical treatment of atrial fibrillation", J. Thorac. Cardiovasc. Surg., 1991, vol. 101, pp. 584-592.
Madden, John L., MD, "Resection of the Left Auricular Appendix", J.A.M.A., Jul. 2, 1949, vol. 140, No. 9, pp. 769-772.
Bonow, Robert O., et al., "Guidelines for the Management of Patients With Valvular Heart Disease: Executive Summary: A Report of the American College of Cardiology/American Heart Association Task Force on Practice Guidelines (Committee on Management of Patients With Valvular Heart Disease)", Circulation J.A.M.A., 1998, vol. 98, pp. 1949-1984.
Halperin, Jonathan L, MD, FACC, et al., "Obliteration of the Left Atrial Appendage for Prevention of Thromboembolism", Journal of the American College of Cardiology, 2003, vol. 42, No. 7, pp. 1259-1261.
Bohm, Jurgen, et al., "Surgical removal of atrial septal defect occlusion system-devices", European Journal of Cardio-thoracic Surgery, 1997, vol. 12, pp. 869-872.
Stollberger, Claudia, MD, et al., "Elimination of the Left Atrial Appendage To Prevent Stroke or Embolism?: Anatomic, Physiologic, and Pathophysiologic Considerations", Chest, Dec. 2003, vol. 124, No. 6, pp. 2356-2362.
Al-Saady, N. M., et al., "Left atrial appendage: structure, function, and role in thromboembolism", Heart, 1999, vol. 82, pp. 547-554.
Sievert, Horst, et al., "Percutaneous Left Atrial Appendage Transcatheter Occlusion to Prevent Stroke in High-Risk Patients With Atrial Fibrillation: Early Clinical Experience", Circulation J.A.M.A., Apr. 23, 2002, pp. 1887-1889.
Coffin, Laurence H., MD, et al., "Use of the Surgical Stapler to Obliterate The Left Atrial Appendage", Surgery, Gynecology & Obstetrics, Jun. 1985, vol. 160, No. 6, pp. 565-566.
Landymore, R., MD, et al., "Staple Closure of the Left Atrial Appendage", The Canadian Journal of Surgery, Mar. 1984, vol. 27, No. 2, pp. 144-145.
Disesa, Verdi J. MD, et al., "Ligation of the Left Atrial Appendage Using an Automated Surgical Stapler", The Annals of Thoracic Surgery, 1988, vol. 46, pp. 652-653.
Japanese Foreign Office Action dated May 10, 2016, issued in corresponding JP Application No. 2015-116009 filed Jun. 8, 2015 (10 pages with English Translation).
EPO Office Action, dated Sep. 9, 2016 in EP Patent Application No. 07761828.8.
Final Office Action dated Nov. 30, 2015 during the prosecution of U.S. Appl. No. 14/047,832, 6 pages.
International Preliminary Report on Patentability issued in International Application No. PCT/US2007/068147, dated Nov. 4, 2008.
International Search Report and Written Opinion issued in International Application No. PCT/US2019/024341, dated Jun. 13, 2019.
Kamohara, Keiji et al., A novel device for left atrial appendage exclusion, The Journal of Thoracic and Cardiovascular Surgery, Dec. 2005, 1639-1644, vol. 130, No. 6.
Office Action issued in CN Application No. 201080042063.3, dated Nov. 15, 2014.
Final Official Action issued in JP Application No. 2012-524852, dated Feb. 6, 2015.
International Search Report and Written Opinion dated Feb. 24, 2015, in corresponding International Patent Application PCT/US2014/066438 filed on Nov. 19, 2014 (13 pages).
Extended European Search Report issued in EP Application No. 10808715.6, dated Mar. 24, 2015.
Office Action issued in CN Application No. 201080042063.3, dated Apr. 9, 2015.
Office Action issued in EP Application No. 07761828.8, dated Apr. 15, 2015.
International Preliminary Report on Patentability issued in International Application No. PCT/US2014/066438, dated May 24, 2016.
Official Action issued in JP Application No. 2015-116009, dated Dec. 16, 2016.
Official Action issued in JP Application No. 2017-049531, dated Dec. 15, 2017.
Office Action issued in U.S. Appl. No. 15/037,963, dated Oct. 18, 2018.
Office Action issued in CN Application No. 201080042063.3, dated Mar. 20, 2014.
Official Action issued in JP Application No. 2012-524852, dated Apr. 1, 2014.
International Preliminary Report on Patentability issued in International Application No. PCT/US2010/045216, dated Feb. 14, 2012.
Office Action issued in U.S. Appl. No. 14/177,027, dated Sep. 30, 2016.
Salzberg, Sacha P., et al., Surgical left atrial appendage occlusion: evaluation of a novel device with magnetic resonance imaging, Eur. J. Cardiothoracic Surg., Aug. 6, 2008, 766-770, 34.
Office Action issued in U.S. Appl. No. 15/165,546, dated Aug. 30, 2018.
Final Office Action issued in U.S. Appl. No. 14/177,027, dated Apr. 5, 2017.
Office Action issued in U.S. Appl. No. 14/177,027, dated Nov. 16, 2017.
Office Action dated May 18, 2015 for corresponding U.S. Appl. No. 14/047,832 (8 pages).

(56) References Cited

OTHER PUBLICATIONS

Restriction Requirement dated Aug. 1, 2018 for parent U.S. Appl. No. 15/037,963, 7 pages.
Notice of Reason for Refusal issued in JP Application No. 2018-047740, dated Oct. 4, 2018.
Notice of Reason for Refusal issued in JP Application No. 2009-510075, dated Feb. 21, 2012.
Notice of Allowance issued in U.S. Appl. No. 12/168,216, dated Aug. 22, 2011.
Partial European Search Report issued in EP Application No. 08170539.4, dated Mar. 26, 2012.
Extended European Search Report issued in EP Application No. 08170539.4, dated Jul. 11, 2012.
Search Report issued in JP Application No. 2008-317561, dated Feb. 18, 2013.
Notice of Reasons of Refusal issued in JP Application No. 2008-317561, dated Mar. 5, 2013.
Decision of Refusal issued in JP Application No. 2008-317561, dated Jan. 7, 2014.
Reconsideration Report by Examiner Before Appeal issued in JP Application No. 2008-317561, dated Jul. 3, 2014.
Notification of Reason for Refusal issued in KR Application No. 20080000430, dated Oct. 30, 2013.
Notice of Final Rejection issued in KR Application No. 20080000430, dated Apr. 11, 2014.
Extended European Search Report issued in EP Application No. 07761828, dated Feb. 3, 2014.
Written Decision on Registration issued in KR Application No. 20080000430, dated Jul. 28, 2014.
Non-Final Office Action issued in U.S. Appl. No. 16/821,608 dated Oct. 28, 2021, 10 pages.
Extended Search Report issued in European Patent Application No. 19777210.6 dated Nov. 11, 2021, 7 pages.

* cited by examiner

DEVICE FOR ATRIAL APPENDAGE EXCLUSION

CROSS-REFERENCE TO RELATED APPLICATION

This application claims priority to U.S. provisional application No. 62/649,455, filed Mar. 28, 2018, which is incorporated herein by reference in its entirety.

BACKGROUND OF THE INVENTION

Field of the Invention

The present disclosure pertains broadly to the field of fasteners and/or applicators. More specifically, the disclosure relates to surgical applicators of implants and/or fasteners, including but not limited to sterilized fasteners such as staples.

Background of the Invention

Atrial fibrillation is a relatively common condition characterized by a very rapid heartbeat of the left and right atrium. While atrial fibrillation is not normally fatal itself, it has been associated with an increased risk of stroke. It is believed that the rapid heartbeat causes blood to pool in the left atrial appendage (LAA) which causes emboli that are released into the left atrium from where they can enter the cerebral vasculature, thus causing a stroke. In addition to stroke, the emboli can enter coronary circulation, potentially causing myocardial infarction, or can enter peripheral circulation, potentially causing peripheral vascular disease.

The risk of stroke in patients suffering from atrial fibrillation can be reduced in a variety of ways. For example, blood thinning drugs can be used to reduce the risk of clot formation. The use of blood thinners, however, is contraindicated in patients at risk of bleeding disorders. More aggressive treatment protocols have been proposed which involve closing the LAA. Closure and excision may be performed in open surgical procedures, typically requiring the patient to be placed on by-pass and the chest to be opened through the sternum. Alternatively, thoracoscopic and other less invasive procedures have been proposed. The tools are used to ablate or fuse the LAA from the inside using energy, adhesives, or the like.

In some examples, a compliant closure structure may be used for closing the LAA. Such compliant structure may have an elastomeric body having a pair of opposed legs which may be arranged in an oval or a U-shaped configuration to define an opening therebetween. By placing the opening between the legs over the LAA and aligning it with the base of the LAA, the compliant closure structure may be closed to provide the desired sealing of the LAA. To hold the compliant closure structure closed, a number of discrete, axially spaced-apart tissue penetrating fasteners are arranged along the lengths of each of the legs. By compressing the legs together to press-fit the closure devices, the compliant closure structure may be closed to provide a compliant seal which effectively isolates the LAA.

The compliant closure structure is closed using a hand-operated delivery tool having jaws which can be inserted into the legs of the closure structure and actuated to close the jaws in the legs over the LAA. The jaws further include comb studs which engage and press fit the closure devices in order to hold the compliant closure structure in its closed, sealing configuration. The studs are intended to be retracted to allow the delivery tool to be removed.

Existing delivery tools have certain shortcomings. For example, the actuation of the jaws and retraction of the comb studs can be performed out of order, increasing the risk that the delivery of the compliant structure will fail. Additionally, existing delivery tools do not allow for repeated "previewing" of the placement of the compliant closure structure on the LAA without closing the tissue penetrating fasteners. Moreover, positioning and orientation of the delivery tool can be difficult, particularly when the tool is introduced through an intercostal penetration to access the LAA.

SUMMARY OF THE INVENTION

For these reasons, it would be desirable to provide improved delivery tools for use with the compliant closure devices for sealing the LAA. It would be further desirable if the delivery tools and methods of their use were compatible with the delivery of other tissue closure devices and for procedures in addition to closure of the LAA.

According to some non-limiting examples, a surgical applicator for a fastener may include a handle, a trigger movable relative to the handle between an initial position, an actuated position, and an intermediate position between the initial position and the actuated position, and a lockout mechanism movable relative to the trigger between a locked position and an unlocked position. The lockout mechanism may be operatively arranged to: lock the trigger in the intermediate position when the trigger is moved from the initial position toward the actuated position, and permit movement of the trigger from the intermediate position toward the initial position or the actuated position when the lockout mechanism is moved from the locked position to the unlocked position.

According to some non-limiting examples, the lockout mechanism may be further operatively arranged to permit movement of the trigger from the initial position to the actuated position when the lockout mechanism is moved from the locked position to the unlocked position prior to movement of the trigger from the initial position. The trigger may be movable relative to the handle from the initial position with application of a compressive force on the trigger in a direction toward the handle. The trigger may have a distal side opposite a proximal side facing the handle, and at least a portion of the lockout mechanism may be positioned on the distal side of the trigger.

According to some non-limiting examples, the lockout mechanism may have a release button connected to the trigger, the release button being movable between a first position and a second position relative to the trigger. The lockout mechanism may further have a trigger stop connected to the handle, the trigger stop being movable between a first position and a second position relative to the handle. The release button may be pivotally movable relative to the trigger, or linearly movable in a direction lateral relative to the trigger. The release button may be biased to the first position by a release button biasing member. The trigger stop may be biased to the first position by a trigger stop biasing member. Movement of the trigger from the initial position toward the actuated position may engage the trigger with the trigger stop to automatically lock the trigger in the intermediate position. Movement of the release button from the first position to the second position when the trigger is in the intermediate position may permit disengagement of the trigger from the trigger stop.

According to some non-limiting examples, a ratcheting mechanism may be provided to engage the trigger when the trigger is moved from the intermediate position toward the actuated position to prevent movement of the trigger toward the initial position. The ratcheting mechanism may disengage from the trigger when the trigger is moved to the actuated position. The ratcheting mechanism may have a ratchet rod and a ratchet that is engaged with the ratchet rod when the trigger is moved from the intermediate position toward the actuated position. The ratcheting mechanism may be actuated when the trigger is moved from the intermediate position toward the actuated position by a predetermined distance.

According to some non-limiting examples, the surgical applicator may further have a jaw assembly selectively movable between an open position and a closed position via movement of the trigger from the initial position to the actuated position. The jaw assembly may have a pair of jaws movably attached to one another, with each jaw having a pair of lateral sides with a plurality of lateral slots extending through each lateral side. An outer surface of at least one of the lateral sides of each jaw may have a recess that receives a cover element for enclosing at least a portion of the plurality of lateral slots. The cover element may be adhesively secured in the recess. The jaws may be pivotally attached to one another by a pin. The surgical application may further include a dampening mechanism operatively arranged with the trigger to dampen variations in a compressive force applied on the trigger during movement between the initial position and the actuated position. The dampening mechanism may have a spring and a damper.

According to some non-limiting examples, a surgical applicator for a fastener may have a handle, a trigger movable relative to the handle between an initial position, an actuated position, and an intermediate position between the initial position and the actuated position, and a lockout mechanism. The lockout mechanism may include a release button connected to the trigger and a trigger stop connected to the handle. Movement of the trigger from the initial position toward the actuated position may engage the trigger stop with the trigger to lock the trigger in the intermediate position, and movement of the release button relative to the trigger when the trigger is in the intermediate position may disengage the trigger from the trigger stop to permit movement of the trigger from the intermediate position toward the initial position or the actuated position. The surgical applicator may further have a ratcheting mechanism that engages the trigger when the trigger is moved from the intermediate position toward the actuated position to prevent movement of the trigger toward the initial position. The ratcheting mechanism may disengage from the trigger when the trigger is moved to the actuated position.

According to some non-limiting examples, a surgical applicator for a fastener may have a handle, a trigger movable relative to the handle between an initial position, an actuated position, and an intermediate position between the initial position and the actuated position, and an elongate body extending distally from the handle. The elongate body may have a distal portion, a jaw assembly at the distal portion selectively movable between an open position, a closed position, and an intermediate position between the open position and the closed position via movement of the trigger. The surgical applicator may further have a lockout mechanism operatively arranged to lock the trigger and the jaw assembly in the intermediate position when the trigger is moved from the initial position toward the actuated position, and permit movement of the trigger from the intermediate position toward the initial position or the actuated position to move the jaw assembly from the intermediate position toward the open position or the closed position, respectively.

According to some non-limiting examples, a method of operating a fastener applicator may include moving a trigger of the fastener applicator from an initial position toward an actuated position by applying a compressive force on the trigger in a direction toward a handle of the fastener applicator, closing a jaw assembly of the fastener applicator from an open position toward a closed position via movement of the trigger, and locking the trigger and the jaw assembly in an intermediate position with a lockout mechanism. The method may further include moving the lockout mechanism from a locked position to an unlocked position, moving the trigger from the intermediate position toward the actuated position, and closing the jaw assembly from the intermediate position to the closed position via movement of the trigger. Closing the jaw assembly to the closed position may close a fastener from an unfixed position to a fixed position.

According to some non-limiting examples, the method may further include blocking the trigger via a ratcheting mechanism from movement toward the initial position after the trigger is moved from the intermediate position toward the actuated position. The jaw assembly may move from the closed position toward the open position when the trigger is moved to the actuated position, or after the trigger is moved to the actuated position. The method may further include unlocking the trigger when the trigger is moved to the actuated position.

Further examples of the present disclosure are set forth in the following numbered clauses.

Clause 1: A surgical applicator for a fastener, the surgical applicator comprising:

a handle;

a trigger movable relative to the handle between an initial position, an actuated position, and an intermediate position between the initial position and the actuated position; and a lockout mechanism movable relative to the trigger between a locked position and an unlocked position, the lockout mechanism operatively arranged to:

lock the trigger in the intermediate position when the trigger is moved from the initial position toward the actuated position; and permit movement of the trigger from the intermediate position toward the initial position or the actuated position when the lockout mechanism is moved from the locked position to the unlocked position.

Clause 2: The surgical applicator of clause 1, wherein the lockout mechanism is further operatively arranged to permit movement of the trigger from the initial position to the actuated position when the lockout mechanism is moved from the locked position to the unlocked position prior to movement of the trigger from the initial position.

Clause 3: The surgical applicator of clause 1 or clause 2, wherein the trigger is movable relative to the handle from the initial position with application of a compressive force on the trigger in a direction toward the handle.

Clause 4: The surgical applicator of any of clauses 1-3, wherein the trigger has a distal side opposite a proximal side facing the handle, and wherein at least a portion of the lockout mechanism is positioned on the distal side of the trigger.

Clause 5: The surgical applicator of any of clauses 1-4, wherein the lockout mechanism comprises:
a release button connected to the trigger, the release button movable between a first position and a second position relative to the trigger, and
a trigger stop connected to the handle, the trigger stop movable between a first position and a second position relative to the handle.

Clause 6: The surgical applicator of clause 4, wherein the release button is pivotally movable relative to the trigger.

Clause 7: The surgical applicator of clause 4, wherein the release button is linearly movable in a direction lateral relative to the trigger.

Clause 8: The surgical applicator of clause 4, wherein the release button is biased to the first position by a release button biasing member.

Clause 9: The surgical applicator of clause 4, wherein the trigger stop is biased to the first position by a trigger stop biasing member.

Clause 10: The surgical applicator of clause 4, wherein movement of the trigger from the initial position toward the actuated position engages the trigger with the trigger stop to automatically lock the trigger in the intermediate position.

Clause 11: The surgical applicator of clause 4, wherein movement of the release button from the first position to the second position when the trigger is in the intermediate position permits disengagement of the trigger from the trigger stop.

Clause 12: The surgical applicator of any of clauses 1-11, further comprising a ratcheting mechanism that engages the trigger when the trigger is moved from the intermediate position toward the actuated position to prevent movement of the trigger toward the initial position.

Clause 13: The surgical applicator of clause 10, wherein the ratcheting mechanism disengages from the trigger when the trigger is moved to the actuated position.

Clause 14: The surgical applicator of clause 10, wherein the ratcheting mechanism comprises a ratchet rod and a ratchet that is engaged with the ratchet rod when the trigger is moved from the intermediate position toward the actuated position.

Clause 15: The surgical applicator of clause 10, wherein the ratcheting mechanism is actuated when the trigger is moved from the intermediate position toward the actuated position by a predetermined distance.

Clause 16: The surgical applicator of any of clauses 1-15, further comprising a jaw assembly selectively movable between an open position and a closed position via movement of the trigger from the initial position to the actuated position.

Clause 17: The surgical applicator of clause 16, wherein the jaw assembly comprises a pair of jaws movably attached to one another, each jaw having a pair of lateral sides with a plurality of lateral slots extending through each lateral side.

Clause 18: The surgical applicator of clause 17, wherein an outer surface of at least one of the lateral sides of each jaw has a recess.

Clause 19: The surgical applicator of clause 18, wherein the recess receives a cover element that encloses at least a portion of the plurality of lateral slots.

Clause 20: The surgical applicator of clause 17, wherein the cover element is adhesively secured in the recess.

Clause 21: The surgical applicator of clause 17, wherein the jaws are pivotally attached to one another by a pin.

Clause 22: The surgical applicator of any of clauses 1-21, further comprising a dampening mechanism operatively arranged with the trigger to dampen variations in a compressive force applied on the trigger during movement between the initial position and the actuated position.

Clause 23: The surgical applicator of clause 22, wherein the dampening mechanism comprises a spring and a damper.

Clause 24: A surgical applicator for a fastener, the surgical applicator comprising:
a handle;
a trigger movable relative to the handle between an initial position, an actuated position, and an intermediate position between the initial position and the actuated position; and
a lockout mechanism comprising a release button connected to the trigger and a trigger stop connected to the handle,
wherein movement of the trigger from the initial position toward the actuated position engages the trigger stop with the trigger to lock the trigger in the intermediate position, and
wherein movement of the release button relative to the trigger when the trigger is in the intermediate position disengages the trigger from the trigger stop to permit movement of the trigger from the intermediate position toward the initial position or the actuated position.

Clause 25: The surgical applicator of clause 24, further comprising a ratcheting mechanism that engages the trigger when the trigger is moved from the intermediate position toward the actuated position to prevent movement of the trigger toward the initial position.

Clause 26: The surgical applicator of clause 24 or clause 25, wherein the ratcheting mechanism disengages from the trigger when the trigger is moved to the actuated position.

Clause 27: A surgical applicator for a fastener, the surgical applicator comprising:
a handle;
a trigger movable relative to the handle between an initial position, an actuated position, and an intermediate position between the initial position and the actuated position;
an elongate body extending distally from the handle, the elongate body having a distal portion;
a jaw assembly at the distal portion of the elongate body, the jaw assembly selectively movable between an open position, a closed position, and an intermediate position between the open position and the closed position via movement of the trigger; and
a lockout mechanism operatively arranged to:
lock the trigger and the jaw assembly in the intermediate position when the trigger is moved from the initial position toward the actuated position; and
permit movement of the trigger from the intermediate position toward the initial position or the actuated position to move the jaw assembly from the intermediate position toward the open position or the closed position, respectively.

Clause 28: A method of operating a fastener applicator, the method comprising:
moving a trigger of the fastener applicator from an initial position toward an actuated position by applying a compressive force on the trigger in a direction toward a handle of the fastener applicator;
closing a jaw assembly of the fastener applicator from an open position toward a closed position via movement of the trigger;
locking the trigger and the jaw assembly in an intermediate position with a lockout mechanism;
moving the lockout mechanism from a locked position to an unlocked position;

moving the trigger from the intermediate position toward the actuated position; and closing the jaw assembly from the intermediate position to the closed position via movement of the trigger.

Clause 29: The method of clause 28, wherein closing the jaw assembly to the closed position closes a fastener from an unfixed position to a fixed position.

Clause 30: The method of clause 28 or clause 29, further comprising blocking the trigger via a ratcheting mechanism from movement toward the initial position after the trigger is moved from the intermediate position toward the actuated position.

Clause 31: The method of any of clauses 28-30, wherein the jaw assembly moves from the closed position toward the open position when the trigger is moved to the actuated position, or after the trigger is moved to the actuated position.

Clause 32: The method of any of clauses 28-31, further comprising unlocking the trigger when the trigger is moved to the actuated position.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Additional advantages and details of the invention are explained in greater detail below with reference to the exemplary examples that are illustrated in the accompanying schematic figures, in which:

In FIGS. 1-13B, like characters refer to the same components and elements, unless otherwise stated.

DESCRIPTION OF THE PREFERRED EXAMPLES

Figure 1:
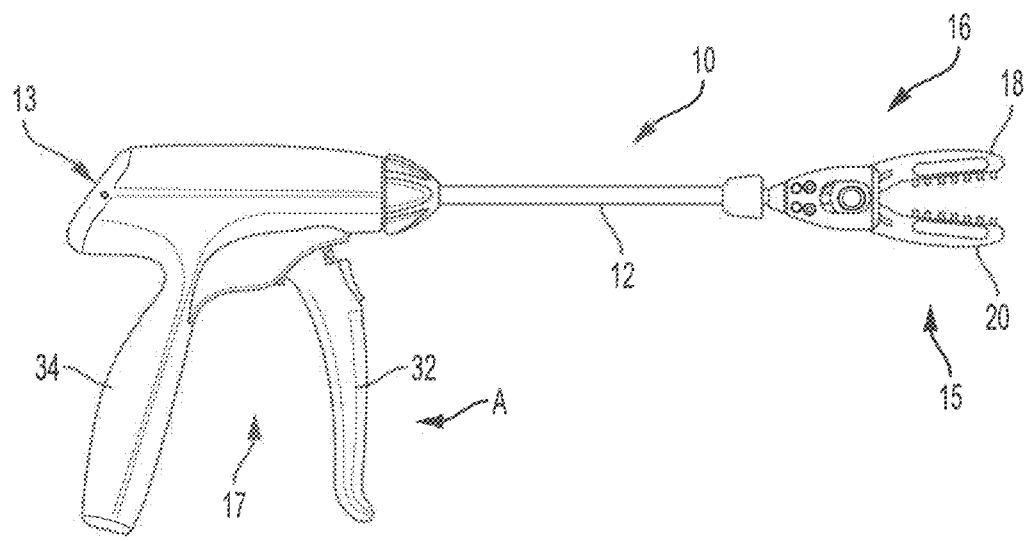
FIG. 1 is a side view of a fastener applicator constructed in accordance with an example of the present disclosure.

Spatial or directional terms, such as "left", "right", "inner", "outer", "above", "below", and the like, are not to be considered as limiting as the invention can assume various alternative orientations. For purposes of the description hereinafter, the terms "end," "upper," "lower," "right," "left," "vertical," "horizontal," "top," "bottom," "lateral," "longitudinal," and derivatives thereof shall relate to the invention as it is oriented in the drawing figures.

As used in the specification and the claims, the singular form of "a," "an," and "the" include plural referents unless the context clearly dictates otherwise.

All numbers used in the specification and claims are to be understood as being modified in all instances by the term "about". By "about" is meant a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The terms "first", "second", and the like are not intended to refer to any particular order or chronology, but instead refer to different conditions, properties, or elements.

By "at least" is meant "greater than or equal to". By "not greater than" is meant "less than or equal to".

The term "includes" is synonymous with "comprises".

The terms "proximal" or "proximally", when used in reference to any portion of the fastener applicator, refer to a portion of the fastener applicator closest to a body of a user handling the fastener applicator during use of the fastener applicator. Conversely, the terms "distal" or "distally", when used in reference to any portion of the fastener applicator, refer to a portion of the fastener applicator furthest away from a body of a user handling the fastener applicator during use of the fastener applicator.

It is to be understood that the specific devices and processes illustrated in the attached drawings, and described in the following specification, are simply exemplary examples or aspects of the invention. Hence, specific dimensions and other physical characteristics related to the examples or aspects disclosed herein are not to be considered as limiting.

Various examples of the present disclosure provide alternative and improved devices, systems, and methods for deploying one or more closure devices or fasteners to tissue. An exemplary tissue structure of a patient at risk of stroke or other adverse events resulting from emboli released into circulation from the LAA, may include the LAA.

Figure 2:
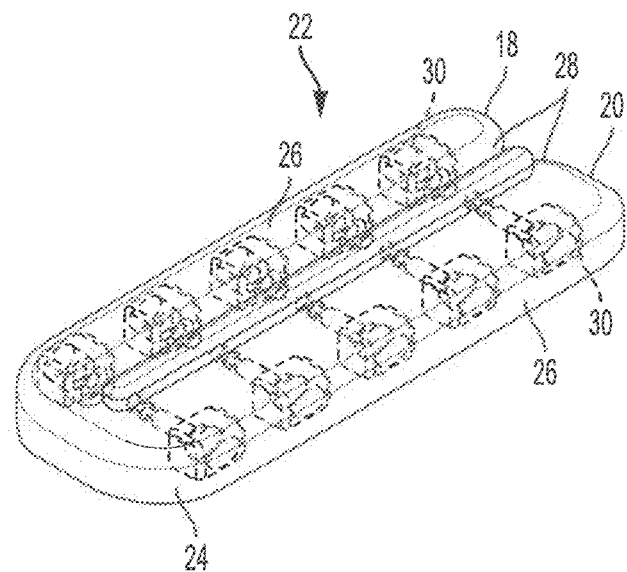
FIG. 2 is a perspective view of a tissue closure device in accordance with an example of the present disclosure.

Referring now to FIG. 1, a fastener applicator 10 (also referred to herein as "surgical applicator" or "applicator") constructed in accordance with various examples of the present disclosure has a shaft 12 having a handle assembly 17 at its proximal end 13, and a jaw assembly 16 at a distal end 15, where individual jaws 18, 20 are adapted to carry a fastener 22 (shown in FIG. 2). The handle assembly 17 has a trigger 32 movable relative to a handle 34 between an initial position, an actuated position, and an intermediate position between the initial position and the actuated position. The trigger 32 is movable relative to the handle 34 from the initial position with application of a compressive force on the trigger 32 in a direction toward the handle 34 (arrow A in FIG. 1). In various examples of the present disclosure, the fastener applicator 10 is configured for introducing the fastener 22 over the tissue structure.

With reference to FIG. 2, the fastener 22 is shown in accordance with one non-limiting example of the present disclosure. The fastener 22 has a substantially U-shaped configuration for receiving the tissue structure, such as the LAA or other tissue structure, when the jaws 18, 20 of the fastener applicator 10 are open. The fastener 22 has a compressible body 24 and a pair of parallel legs 26 having two opposed compliant tissue-engaging surfaces 28. The legs 26 are movable between an open or unfixed position and a closed or fixed position. In some examples, the legs 26 are each comprised of a soft biologically compatible material. The fastener 22 further has a plurality of tissue-penetrating fasteners 30 spaced-apart along the legs 26 and disposed to extend from a first one of the tissue-engaging surfaces 28, through tissue at a puncture site, to a second one of the tissue-engaging surfaces 28 to close the tissue structure therebetween. The plurality of tissue-penetrating fasteners 30 apply a desired level of compression force, which is determined by both the softness of the compressible body 24 and the distance between the tissue-engaging surfaces 28 when they are fully connected to the tissue structure. When connected to the tissue structure, the fastener 22 is left in place in order to close and/or seal the tissue structure. A portion of the tissue structure extending beyond the fastener 22 may then be cut, excised, or otherwise removed, although this may be left to the physician's preference. More detailed description of various fasteners suitable for use with the fastener applicator 10 of the present disclosure are described in U.S. Pat. No. 7,992,757, the full disclosure of which is incorporated herein by reference.

Figure 3:
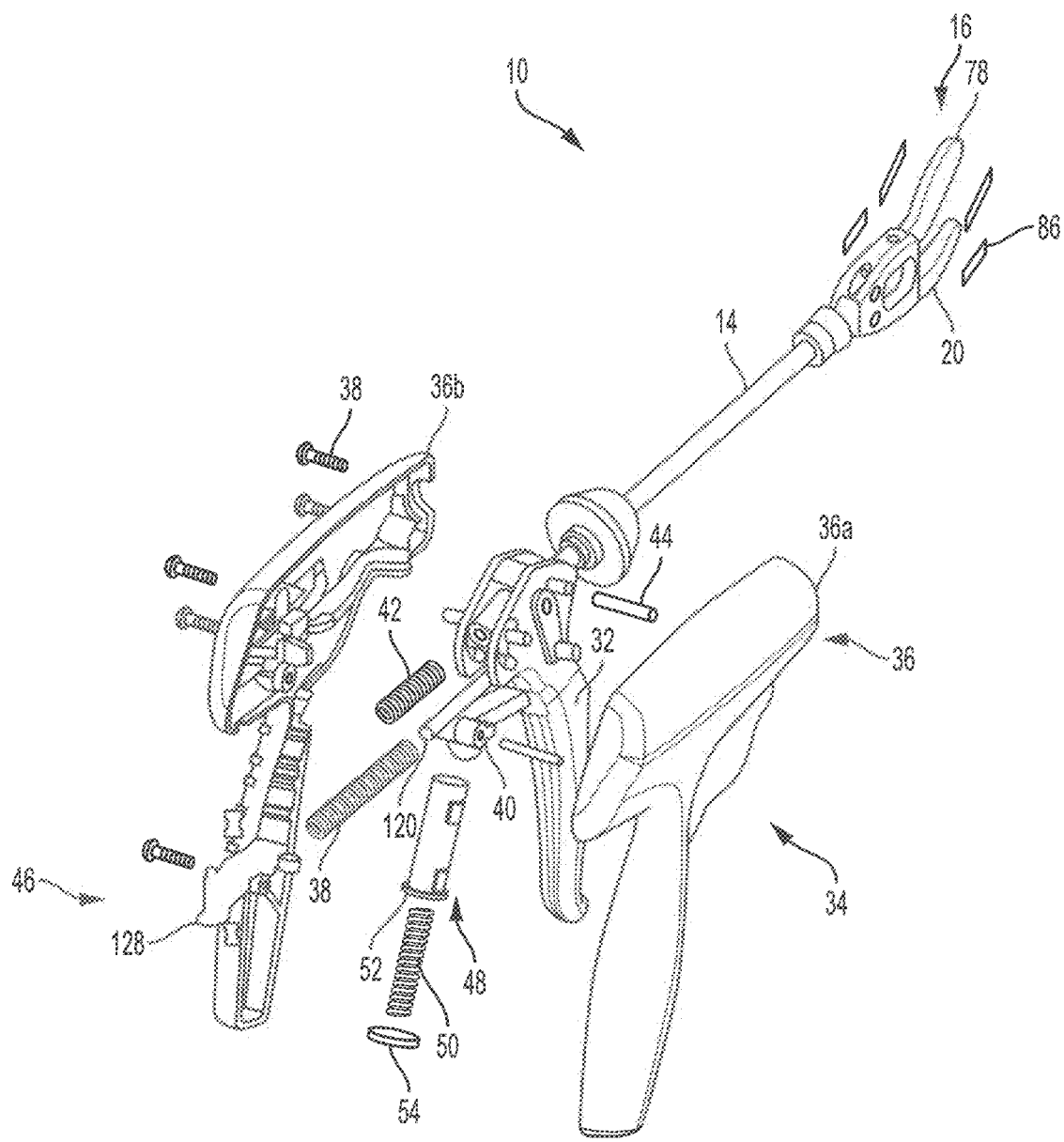
FIG. 3 is an exploded perspective view of the fastener applicator shown in FIG. 1.

Referring now to FIG. 3, an exploded view of the fastener applicator 10 of FIG. 1 is shown. The handle assembly 17 has a housing 36 comprising a first housing portion 36a and a second housing portion 36b coupled to one another and defining an interior space for receiving the working components of the handle assembly 17. The first housing portion 36a and the second housing portion 36b, when assembled together, define the handle 34 that is grasped by the user when handling the fastener applicator 10. In some examples, the first and second portions 36a, 36b of the housing 36 are coupled using one or more handle fasteners 38. In other examples, the first and second portions 36a, 36b of the housing 36 may be coupled using clips, grooves, adhesive, welding, or any other mechanical fastening arrangement. In various examples, the first and second portions 36a, 36b of the housing 36 may be removably or non-removably coupled to one another.

With continued reference to FIG. 3, the interior space of the housing 36 receives various components for actuating the surgical applicator 10 between an initial position, an actuated position, and an intermediate position between the initial position and the actuated position. For example, the housing 36 may receive various gears, linkages, springs, or the like to effect movement or actuation of the trigger 32 between the initial position, the actuated position, and the intermediate position between the initial position and the actuated position. As discussed herein, the housing 36 receives at least a portion of the trigger 32 that is movable relative to the housing 36 in a pivoting motion about a trigger pivot pin 44. The trigger 32 may be biased to the initial position by a trigger biasing member, such as a trigger spring 38. The trigger spring 38 is compressible with movement of the trigger 32 from the initial position such that a restoring force is generated in the trigger spring 38 that restores the trigger 32 to the initial position when an urging force on the trigger 32 is removed or reduced to a magnitude that is lower than the restoring force of the trigger spring 38. In some examples, the trigger 32 has a trigger stop 40 pivotally connected to at least a portion of the housing 36. The trigger stop 40 may be movable between a first position and a second position relative to the handle 34. The trigger stop 40 is biased to the first position by a trigger stop biasing member, such as a dampening spring 50.

With continued reference to FIG. 3, the housing 36 receives a ratcheting mechanism 46 having a ratchet rod 120 and a ratchet 128, as discussed herein. The ratcheting mechanism 46 engages when the trigger 32 is moved from the intermediate position toward the actuated position to prevent movement of the trigger 32 toward the initial position. In some examples, the ratcheting mechanism 46 disengages when the trigger 32 reaches the actuated position such that the trigger 32 automatically moves toward the initial position when the ratcheting mechanism 46 is disengaged, or when the force applied to the trigger is relieved. A dampening mechanism 48 is received within the housing 36 and operatively arranged with the trigger 32 to dampen variations in a compressive force applied on the trigger 32 during movement between the initial position and the actuated position. In some examples, the dampening mechanism 48 has a dampening spring 50 received within a damper plunger 52 and a damper 54. In various examples, the damper 54 may be a friction damper, an elastomeric damper, a magnetic damper, a viscous damper, or any combination thereof.

Figure 4A:
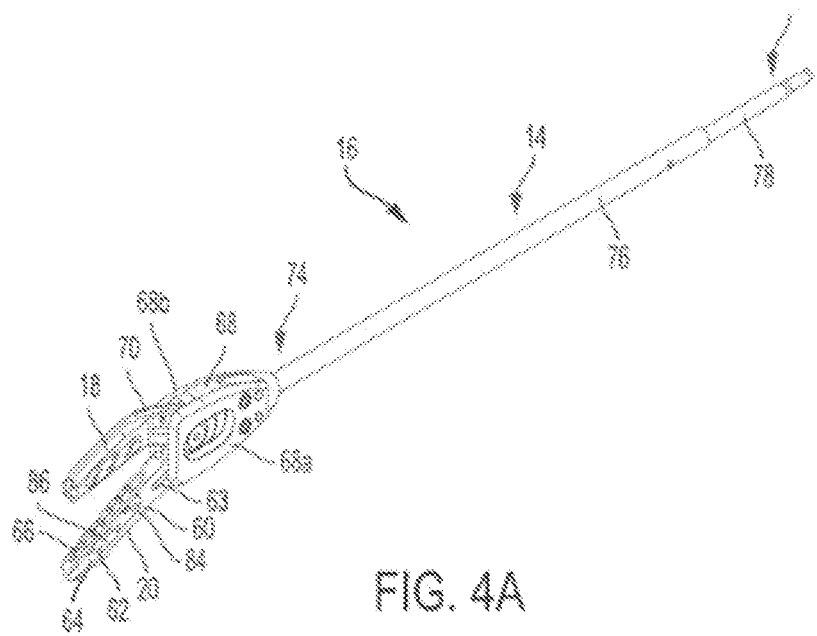
FIG. 4A is a perspective view of a pull rod assembly of the fastener applicator shown in FIG. 1.
Figure 4B:
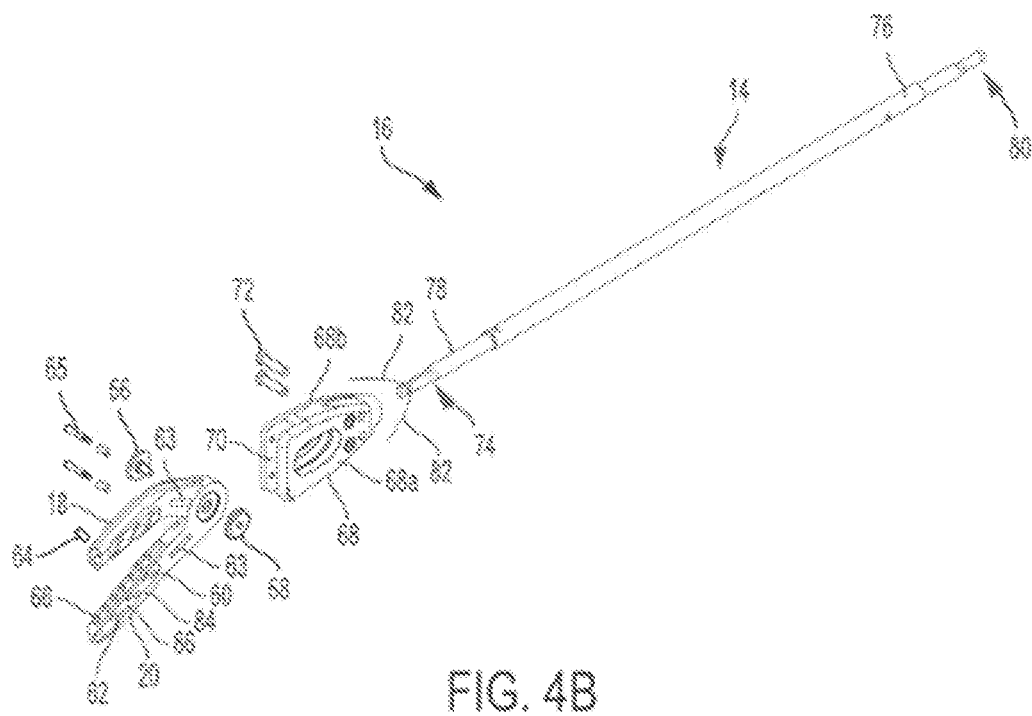
FIG. 4B is an exploded perspective view of the pull rod assembly shown in FIG. 4A.

With reference to FIG. 4A, the jaw assembly 16 is illustrated separate from the remaining components of the fastener applicator 10. FIG. 4B is an exploded view of the jaw assembly 16 of FIG. 4A. As described herein, the jaw assembly 16 is movable between an open position (shown in FIGS. 4A-4B) and a closed position (shown in FIGS. 8B-8C) via movement of the trigger 32 from the initial position to the actuated position. The jaw assembly 16 comprises a pair of jaws 18, 20 movably attached to one another. In some examples, the jaws 18, 20 are pivotally attached to one another with a hinge pin 56 and a washer 58. In some examples, the hinge pin 56 and the washer 58 may be welded together, such as using laser welding, ultrasonic welding, or other type of welding. In other examples, the hinge pin 56 and the washer 58 are adhesively connected with each other, threadably connected with each other, or connected by way of any other removable or non-removable mechanical connection.

With continued reference to FIGS. 4A-4B, each jaw 18, 20 has a pair of lateral sides 60, with each lateral side 60 having a plurality of lateral slots 62 extending therethrough. The lateral slots 62 define a channel for guiding the movement of jaw cam pins 64. A single jaw cam pin 64 is received within each lateral slot 62 and is movable within the lateral slot 62 between a first position and a second position. In the first position, the jaw cam pins 64 in each jaw 18, 20 are positioned relative to a stud comb 66 such that the comb 66 is in an extended or exposed position within the jaws 18, 20. In the second position, the jaw cam pins 64 in each jaw 18, 20 are positioned such that the jaw cam pins 64 urge the stud comb 66 in each jaw 18, 20 to a retracted or concealed position, wherein the comb 66 acts on the tissue penetrating fasteners 30 of the fastener 22.

With continued reference to FIGS. 4A-4B, the jaws 18, 20 are received within a clamp box 68. In some examples, the clamp box 68 has a pair of sides 68a, 68b defining a central opening 70 therebetween for receiving the jaws 18, 20. The sides 68a, 68b of the clamp box 68 may be removably or non-removably connected to one another, such as by one or more rivets 72. The movement of the jaws 18, 20 between the open and closed positions is guided by the interaction between the guide slots 63 on each of the jaws 18, 20 and a corresponding guide pin 65 (shown in FIG. 4B) on the clamp box 68.

Figure 4C:
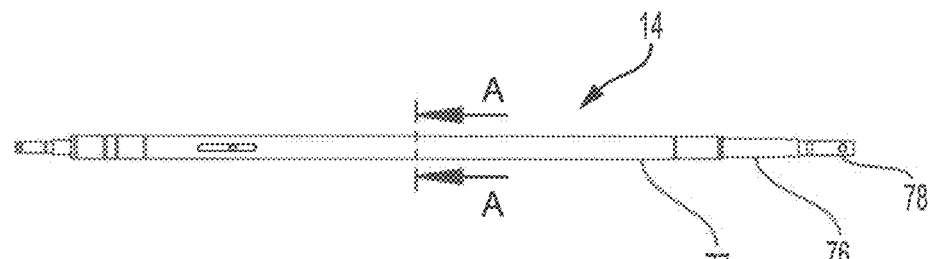
FIG. 4C is a top view of a shaft of a pull rod assembly.
Figure 4D:
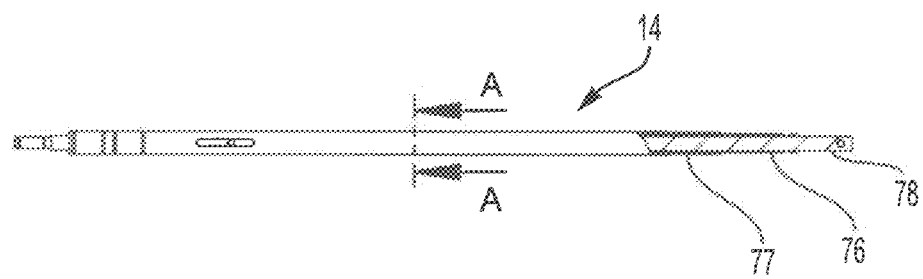
FIG. 4D is a top partial cross-sectional view of the shaft shown in FIG. 4C.
Figure 4E:
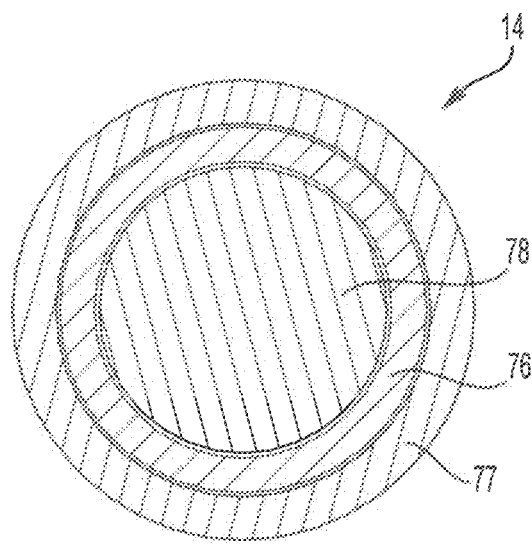
FIG. 4E is a cross-sectional view of the shaft shown in FIGS. 4C-4D taken along line A-A.

The clamp box 68 receives a distal end 74 of at least a portion of the shaft 14, such as the distal end of the clamp tube 76. With reference to FIGS. 4C-4E, the shaft 14 comprises the clamp tube 76 slidably received within an ejection tube 77 and an inner pull rod 78 slidably received within the clamp tube 76 such that the clamp tube, ejection tube 77, and the inner pull rod 78 are coaxially disposed relative to one another. The clamp tube 76 may be rotatable about its longitudinal axis to rotate the clamp box 68 and the jaws 18, 20, thereby facilitating the orientation of the jaws 18, 20 relative to the handle assembly 17 during use of the fastener applicator 10. In some examples, the shaft 14 is rotatable about its longitudinal axis with rotation of the positioning knob 88 (shown in FIG. 5).

The pull rod 78 is axially movable relative to the clamp tube 76 with movement of the trigger 32. For example, the pull rod 78 may be movable in a direction extending between the proximal and distal ends of the shaft 14 and along a longitudinal axis thereof. Movement or closure of the trigger 32 from the initial position toward the actuated position draws the pull rod 78 proximally toward a proximal end 80 of the shaft 14 relative to the clamp tube 76 and the ejection tube 77, which in turn closes the jaws 18, 20. The ejection tube 77 has at least one tendon 82 connected at its distal end. The at least one tendon 82 is operatively connected with the comb stud 66 such that movement of the trigger 32 to the activated position also pulls the at least one tendon 82 to cause the retraction of the comb stud 66.

With reference to FIGS. 4A-4B, an outer surface of at least one of the lateral sides 60 of each jaw 18, 20 has a recess 84. The recess 84 may be formed as a channel that extends into the body of each jaw 18, 20 from the lateral sides 60 in a region surrounding the lateral slots 62. In some examples, the recess 84 receives a cover element 86 (also shown in FIG. 3) that encloses at least a portion of the plurality of lateral slots 62. A thickness of the cover element 86 may be chosen such that an outer surface of the cover element 86 may be flush with the surface of the lateral side 60. In other examples, the thickness of the cover element 86 may be chosen such that its outer surface is recessed relative to the surface of the lateral side 60, or such that the outer surface of the cover element 86 protrudes laterally from the surface of the lateral side 60. In some examples, the cover element 86 may be adhesively secured in the recess 84. In further examples, the cover element 86 may be transparent such that the lateral slots 62 and the jaw cam pins 64 can be seen through the cover element 86. When positioned in the recess 84, the cover element 86 prevents contamination of the lateral slots 62 and the jaw cam pins 64 during use of the fastener applicator 10 which may cause the blockage of one or more lateral slots 62 and/or impede the movement of one or more jaw cam pins 64 through the lateral slots 62.

Figure 5:
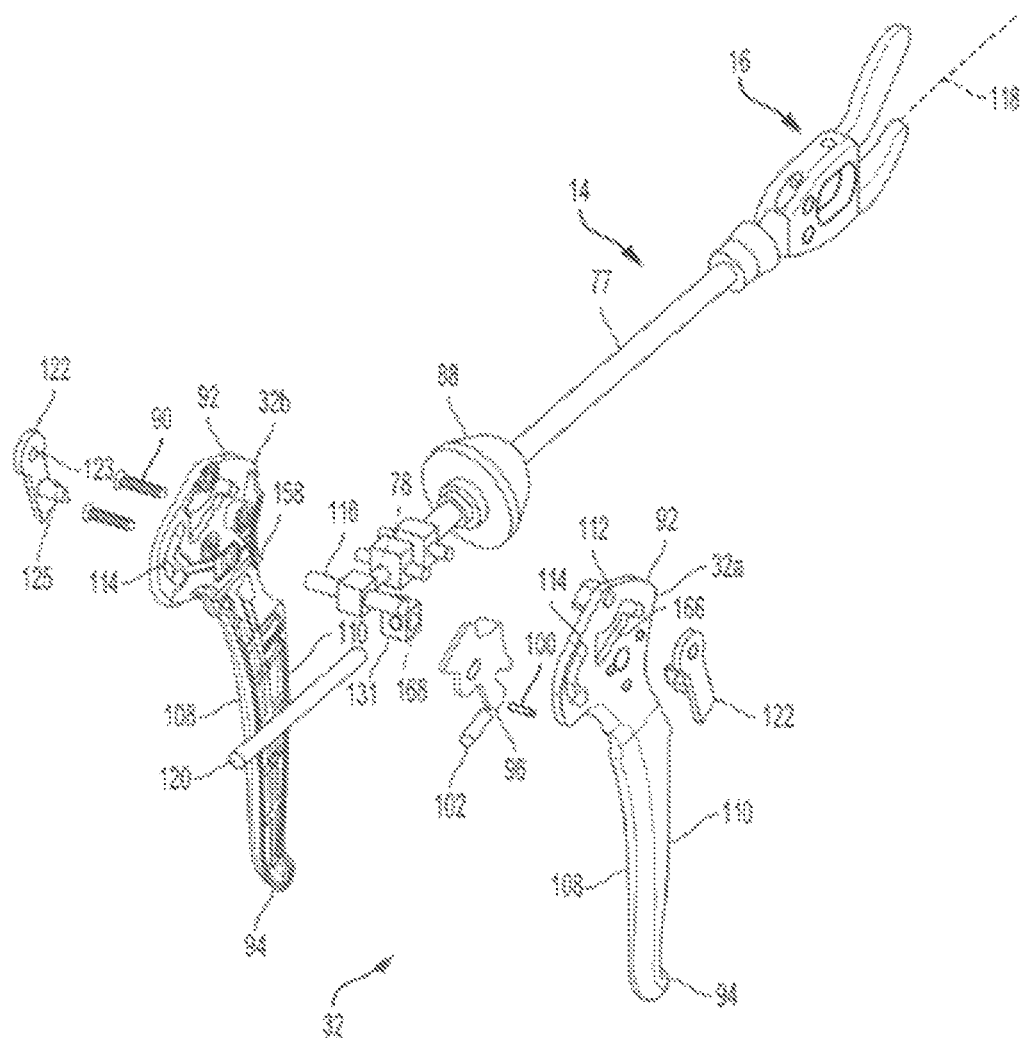
FIG. 5 is an exploded perspective view of a trigger assembly of the fastener applicator shown in FIG. 1.

With reference to FIG. 5, the trigger 32 comprises a first trigger portion 32a and a second trigger portion 32b coupled to one another. The first trigger portion 32a and the second trigger portion 32b, when assembled together, define the trigger 32 that is grasped by the user when handling the fastener applicator 10. In some examples, the first and second trigger portions 32a, 32b are coupled using one or more trigger fasteners 90. In other examples, the first and second trigger portions 32a, 32b may be coupled using clips, grooves, adhesive, welding, press fit, or any other mechanical fastening arrangement. In various examples, the first and second trigger portions 32a, 32b may be removably or non-removably coupled to one another.

With continued reference to FIG. 5, each trigger portion 32a, 32b has a first end 92 that is received within the housing 36 (shown in FIG. 3) and pivotally movable relative to the housing 36. A second free end 94 extends opposite the first end 92 and protrudes outside the housing 36. The second free end 94 of the trigger 32 is configured for being grasped by the user during movement of the trigger 32 between the initial position and the activated position. The trigger 32 further has a distal side 110 opposite a proximal side 108 facing the handle. As described herein, at least a portion of a lockout mechanism is positioned on the distal side 110 of the trigger 32.

Figure 7A:
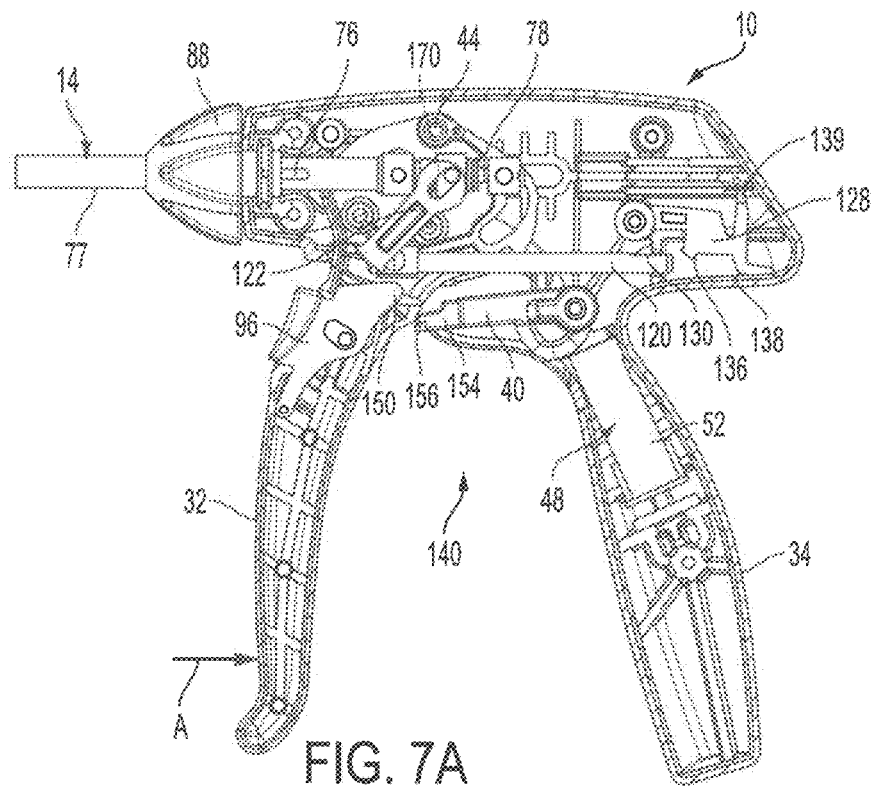
FIG. 7A is a side view of the trigger assembly of the fastener applicator shown in FIG. 1, showing a trigger in an initial position.
Figure 10A:
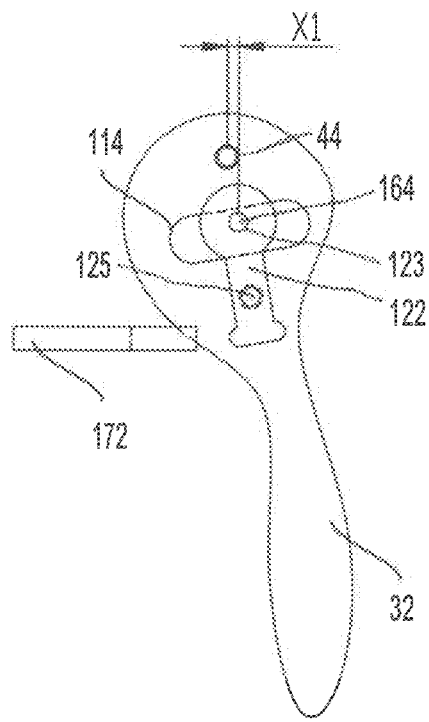
FIGS. 10A-10C are schematic views of a trigger and a trigger sub lever illustrating the movement of the trigger between an initial position and an actuated position according to an example of the present disclosure.
Figure 10B:
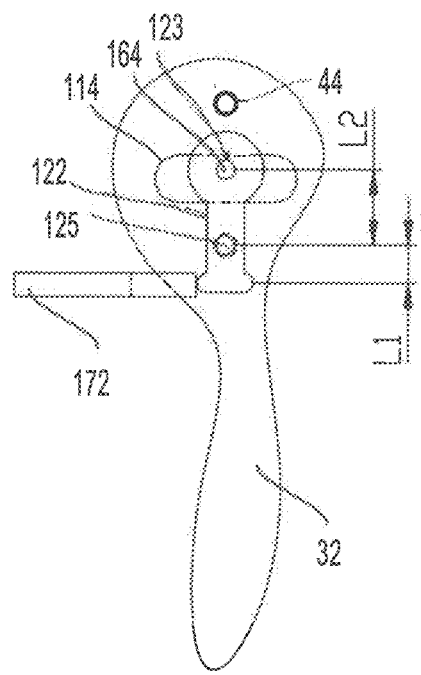

With continued reference to FIG. 5, the trigger 32 has a pivot pin opening 112 configured for receiving the trigger pivot pin 44 (shown in FIG. 3). The trigger 32 is pivotally movable about a longitudinal axis of the trigger pivot pin 44 which has its terminal ends secured to the housing 36. A trigger slot 114 extends through the body at the first end 92 of the trigger 32. The trigger slot 114 is configured to receive a closing trunnion 116 connected to the distal end of the pull rod 78. The trigger slot 114 acts as a camming mechanism for controlling the movement of the pull rod 78 due to the movement of the closing trunnion 116 within the trigger slot 114. In some examples, the shape of the trigger slot 114 is configured to result in a linear movement of the pull rod 78 in a direction of a longitudinal axis 118 of the shaft 14 as a result of a pivoting movement of the trigger about the trigger pivot pin 44. The closing trunnion 116 may contact or be positioned in near contact with a first end of the trigger slot 114 when the trigger 32 is in the initial position (FIG. 7A). Similarly, the closing trunnion 116 may contact or be positioned in near contact with a second end (opposite the first end) of the trigger slot 114 when the trigger 32 is in the actuated position (FIG. 7E). The closing trunnion 116 may be positioned between the first end and the second end of the trigger slot 114 when the trigger 32 is in the intermediate position between the initial position and the actuated position. Lateral pins of an ejection trunnion 164 are received within an opening 123 extending through a first end of a trigger sub lever 122 (see, also, FIGS. 10A-10C) such that movement of the trigger 32 also causes a corresponding movement of the trigger sub lever 122 due to movement of the ejection trunnion 164 within the trigger slot 114 (see FIGS. 10A-10C).

With continued reference to FIG. 5, a second end of the trigger sub lever 122 has a pin 125 that is pivotally connected to the trigger 32. In this manner, the first end of the trigger sub lever 122 is slidably movable relative to the trigger slot 166 and the ejection trunnion 164, while the second end of the trigger sub lever 122 is pivotally movable relative to the trigger sub stop feature 172 on the handle 34 (see FIGS. 10A-10C). When the second end of trigger sub lever 122 strikes the trigger sub stop feature 172 on the handle 34, and the trigger 32 continues moving proximally toward an actuated position, relative motion of the first end of the trigger sub lever 122 is amplified by pivoting about a pin 125. Amplification is determined by the ratio of the two distances L1 and L2 in FIG. 10B. L1 is the distance between the trigger sub stop feature 172 and the trigger sub lever pin 125 while L2 is the distance between the trigger sub lever pin 125 and the ejection trunnion 164. The trigger sub lever 122 effects the ejection trunnion 164 via the trigger sub lever slot 170. In this manner, a first (small) movement of the trigger 32 can have a second (greater) movement on the ejection trunnion 164 due to the ejection trunnion 164 being linked to the ejection tube 77. In this manner, the combs 66 can be retracted via the tendons 82 to release the fastener 22 (shown in FIG. 2).

Figure 6A:
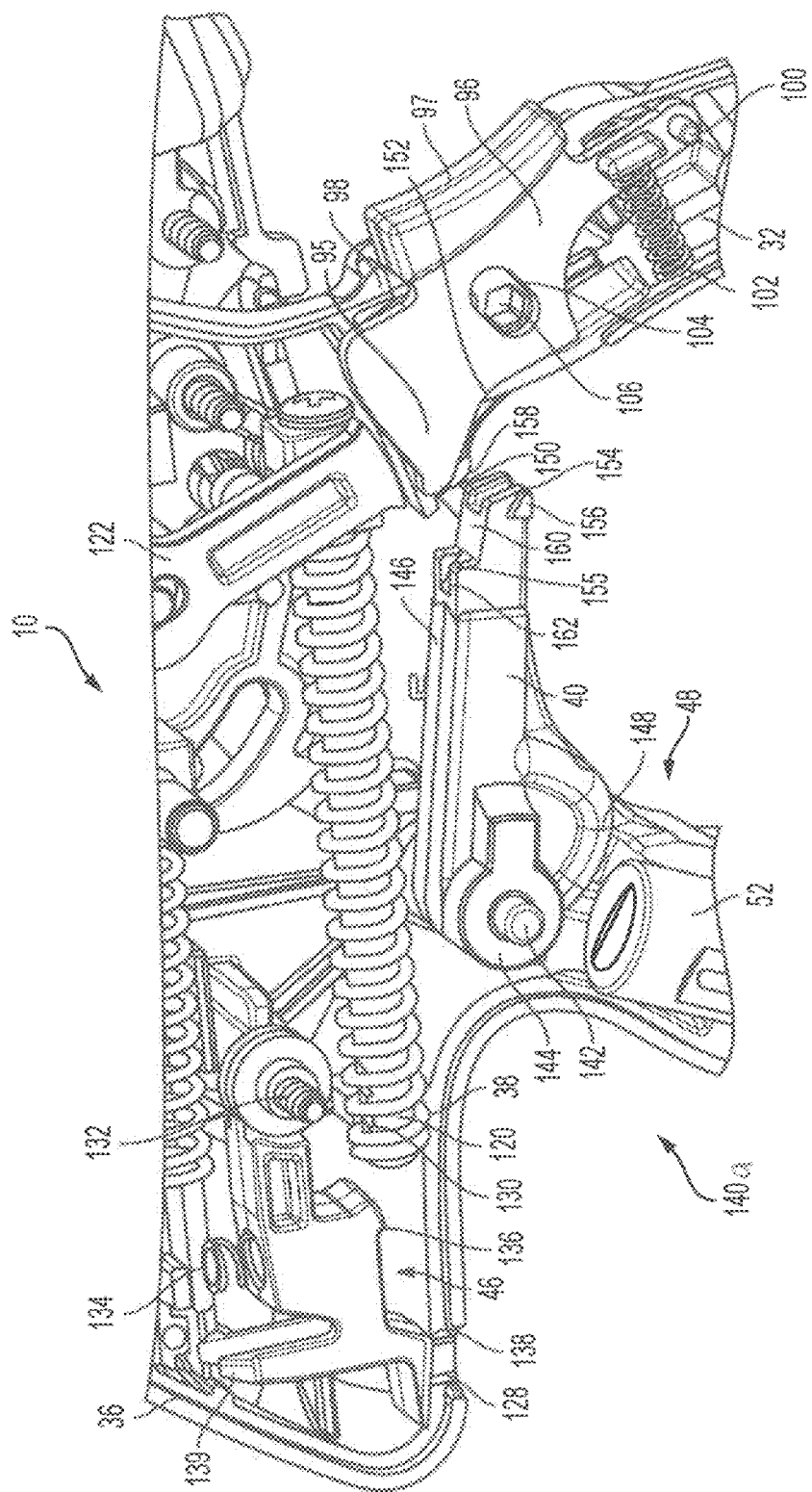
FIG. 6A is a detailed perspective view of a trigger release button and trigger stop of a fastener applicator in accordance with an example of the present disclosure.

With reference to FIG. 6A, the fastener applicator 10 has a lockout mechanism 140a movable relative to the trigger 32 between a locked position and an unlocked position. The lockout mechanism 140a in FIG. 6A is shown in accordance with one example of the present disclosure. The lockout mechanism 140a is operatively arranged to lock the trigger 32 in the intermediate position (FIG. 7B) when the trigger 32 is moved from the initial position toward the actuated position. The lockout mechanism 140a is further operatively arranged to permit movement of the trigger 32 from the intermediate position toward the initial position or the actuated position when the lockout mechanism is moved from the locked position to the unlocked position (FIG. 7C). The lockout mechanism 140a is further operatively arranged to lock the trigger 32 in the initial position when a trigger release button 96 is moved from the first position to the second position prior to movement of the trigger 32 from the initial position.

With continued reference to FIG. 6A, the lockout mechanism 140a comprises the trigger release button 96, the trigger stop 40, and the ratcheting mechanism 46. As described herein, movement of the trigger 32 from the initial position toward the actuated position engages the trigger 32 with the trigger stop 40 and moves the trigger stop 40 to automatically lock the trigger 32 in the intermediate position. To release the trigger 32 from the intermediate position, movement of the trigger release button 96 from the first position to the second position about the trigger release button pivot pin 100 when the trigger 32 is in the intermediate position permits disengagement of the trigger stop 40 from the trigger 32. In this manner, the trigger 32 can be retracted to the initial position due to a restoring force of the trigger spring 38 or moved to the actuated position to close the fastener 22 (shown in FIG. 2).

The trigger release button 96 extends through an opening 98 on the trigger 32 between the first end 92 and the second free end 94 (FIG. 5). In various examples, the trigger release button 96 is positioned relative to the first and second ends 92, 94 of the trigger 32 such that the trigger release button 96 may be operated using the user's index finger that contacts a pressing surface 97 of the trigger release button 96. The trigger release button 96 is movable between a first position, wherein the trigger release button 96 protrudes from the opening 98, and a second position, wherein at least a portion of the trigger release button 96 is moved into the opening 98 on the trigger. In some examples, the trigger release button 96 may protrude from the opening 98 in the first position and the second position.

The trigger release button 96 is pivotally movable relative to the trigger 32 between the first position and the second position about the first trigger release button pivot pin 100. In other examples, the trigger release button 96 may be linearly movable relative to the trigger 32, such as by movement in a proximal/distal direction of the fastener applicator 10, or in a lateral direction relative to the trigger 32. A trigger release button slot 104 in the trigger release button 96 receives a second trigger release button pin 106 and may delimit a range of movement of the trigger release button 96. The second trigger release button pin 106 may contact or be positioned in near contact with a first end of the trigger release button slot 104 when the trigger release button 96 is in the first position. Similarly, the second trigger release button pin 106 may contact or be positioned in near contact with a second end (opposite the first end) of the trigger release button slot 104 when the trigger release button 96 is in the second position.

The trigger release button 96 is biased to the first position by a release button biasing member, such as a trigger release button spring 102. The trigger release button spring 102 is compressible with movement of the trigger release button 96 from the first position toward the second position such that a restoring force is generated in the trigger release button spring 102 that restores the trigger release button 96 to the first position when an urging force on the trigger release button 96 is removed and the trigger release button 96 is disconnected from the trigger stop 40.

With continued reference to FIG. 6A, the trigger release button 96 has a stop member 150 positioned at a second free end 95 of the trigger release button 96 and configured for engaging at least a portion of the trigger stop 40 to prevent movement of the trigger 32 from the initial position if the trigger release button 96 is pressed before the trigger 32 is moved to the intermediate position. In this manner, the trigger 32 can be moved from the initial position only if the trigger release button 96 is not pressed. In some examples, the stop member 150 may be configured as a rounded tip at the second end of the trigger release button 96.

With continued reference to FIG. 6A, the trigger release button 96 has a trigger stop release member 152 positioned between the first trigger release button pivot pin 100 and the stop member 150. The trigger stop release member 152 is configured for engaging at least a portion of the trigger stop 40 when the trigger 32 is positioned in the intermediate position between the initial position and the actuated position. Pressing the trigger release button 96 when the trigger 32 is in the intermediate position engages the trigger stop release member 152 with the trigger stop 40 to unlock the trigger stop 40 and permit movement of the trigger 32 from the intermediate position toward the actuated position or the initial position. In some examples, the trigger stop release member 152 may be shaped as a rounded protrusion at a proximal portion of the trigger release button 96 between the first trigger release button pivot pin 100 and the stop member 150.

Figure 11:
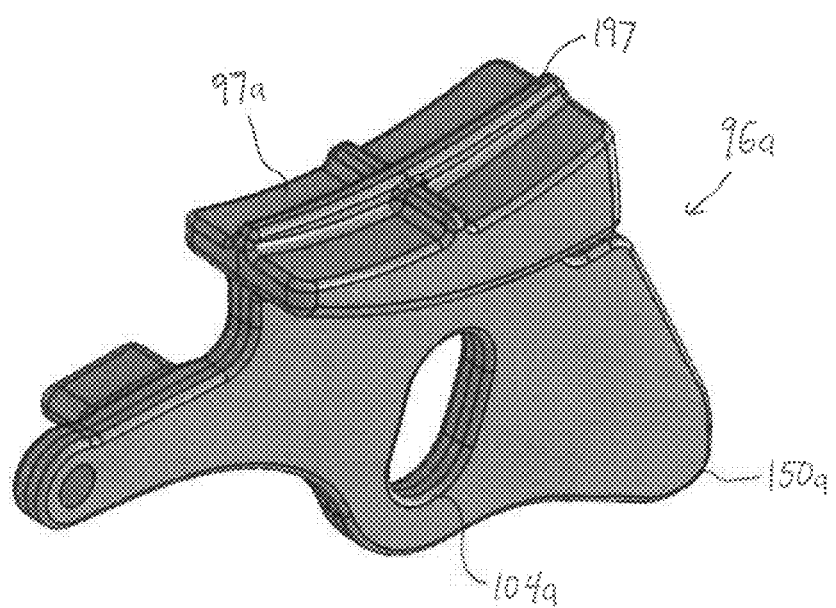
FIG. 11 is a perspective view of a trigger release button in accordance with an example of the present disclosure.

A non-limiting example embodiment of a trigger release button 96a is shown in FIG. 11. The embodiment of the trigger release button 96a includes a pressing surface 97a, a trigger release button slot 104a, and a stop member 150a. In the embodiment of the trigger release button 96a shown in FIG. 11, the pressing surface 97a includes a raised cross pattern 197, which provides a distinct surface for the user to locate the trigger release button and an increased grip to the user, thereby making the fastener applicator easier to use. This non-limiting example embodiment of trigger release button 96a can be used in the embodiments of the fastener applicator of the present disclosure, including the embodiments of the fastener applicator shown in FIGS. 6A, 6B and 7A-7E.

With continued reference to FIG. 6A, the trigger stop 40 is connected to the handle 34 and is movable relative to the handle 34 between a first position (FIG. 7A) and a second position (FIG. 7E). The trigger stop 40 is biased to the first position by a trigger stop biasing member, such as the dampening spring 50 (FIG. 3). In some examples, the trigger stop 40 is pivotally movable relative to the handle 34 between the first position and the second position about a trigger stop pin 142. The trigger stop 40 has a first end 144 that is pivotable about the trigger stop pin 142 and a second free end 146 opposite the first end 144.

At least a portion of the trigger stop 40 may be recessed within the housing 36 of the handle 34 when the trigger stop 40 is in the first position. For example, the first end 144 and the second end 146 of the trigger stop 40 may be recessed within the housing 36 of the handle 34 when the trigger stop 40 is in the first position. In some examples, at least a portion of the trigger stop 40 may extend from the housing 36 of the handle 34 when the trigger stop 40 is pivoted from the first position toward the second position. For example, the first end 144 of the trigger stop 40 may be recessed within the interior of the housing 36 of the handle 34 while at least a portion of the second end 146 of the trigger stop 40 protrudes from the interior of the housing 36 when the trigger stop 40 is pivoted from the first position toward the second position.

With continued reference to FIG. 6A, the trigger stop 40 has a dampening cam 148 configured for interacting with the dampening mechanism 48 when the trigger 32 is moved from the intermediate position toward the actuated position. The dampening cam 148 is positioned at the first end 144 of the trigger stop 40 and is shaped to vary the displacement of the dampening spring 50 (shown in FIG. 3) and the dampening plunger 52 during the stroke of the trigger 32 between the intermediate position toward the actuated position. As the dampening plunger 52 is compressed against the restoring force of the dampening spring 50, the dampening plunger 52 engages the damper 54 (shown in FIG. 7E). In some examples, the dampening cam 148 on the trigger stop 40 and the dampening mechanism 48 may be configured to require a persistent resistive force on the trigger 32 during movement of the trigger 32 from the intermediate position toward the final position regardless of the position of the trigger 32 during its stroke between the intermediate position and the final position. In this manner, the user does not need to vary the force input on the trigger 32 during activation of the fastener applicator 10 which may inadvertently change the position of the jaw assembly 16 (shown in FIG. 1) relative to the tissue structure.

With continued reference to FIG. 6A, the second end 146 of the trigger stop 40 has a first stop member engagement surface 154 configured for engaging the stop member 150 of the trigger release button 96 if the trigger release button 96 is pressed while the trigger 32 is positioned in the initial position. Contact between the first stop member engagement surface 154 of the trigger stop 40 and the stop member 150 of the trigger release button 96 prevents movement of the trigger 32 from the initial position toward the actuated position if the trigger release button 96 is pressed before the trigger 32 is moved to the intermediate position. In this manner, the trigger 32 is locked in the initial position until the trigger release button 96 is released, thereby disengaging the first stop member engagement surface 154 of the trigger stop 40 from the stop member 150 of the trigger release button 96. In some examples, the first stop member engagement surface 154 of the trigger stop 40 may be configured as a recess at a terminal portion of the second end 146 of the trigger stop 40.

Movement of the trigger 32 to the intermediate position locks the trigger 32 relative to the handle 34 due to engagement of a trigger latch 156 on the trigger stop 40 with a trigger catch 158 on the trigger 32. In some examples, the trigger latch 156 on the trigger stop 40 is configured as at least one protrusion that extends laterally away from at least one lateral side of the trigger stop 40. In some examples, the trigger latch 156 is a pair of protrusions that extend laterally away from opposing lateral sides of the trigger stop 40. The trigger catch 158 on the trigger 32 may be configured as a recess on a proximal side 108 of the trigger 32 that is shaped to receive at least a portion of the trigger latch 156.

The trigger latch 156 and the trigger catch 158 engage when the trigger 32 is moved to the intermediate position and prevent movement of the trigger 32 toward the initial position or the actuated position. The trigger latch 156 and the trigger catch 158 are disengaged by pressing the trigger release button 96, whereby at least a portion of the trigger release button 96 contacts at least a portion of the trigger stop 40 to move the trigger stop 40 and displace the trigger latch 156 from contact with the trigger catch 158 on the trigger 32. In some examples, the stop member 150 of the trigger release button 96 engages a release surface 160 on the trigger stop 40 to move the trigger stop 40 and displace the trigger latch 156 from contact with the trigger catch 158 on the trigger 32. The release surface 160 may be positioned at the second end 146 of the trigger stop 40 and proximally of the stop member 150.

With continued reference to FIG. 6A, the trigger stop 40 has a trigger actuation surface 162 positioned proximally of a second stop member engagement surface 155 and the release surface 160. The trigger actuation surface 162 of the trigger stop 40 is configured for engaging the trigger stop release member 152 of the trigger release button 96 when the trigger 32 is moved from the intermediate position toward the actuated position while the trigger release button 96 is pressed. Pressing the trigger release button 96 when the trigger 32 is moved from the intermediate position toward the actuated position engages the trigger stop release member 152 with the trigger actuation surface 162 of the trigger stop 40 to unlock the trigger stop 40 and permit movement of the trigger 32 toward the actuated position. In some examples, the trigger actuation surface 162 may be shaped as a ramp that engages the trigger stop release member 152 of the trigger release button 96. In examples where the trigger actuation surface 162 is shaped as a slot, the trigger actuation surface 162 provides clearance for movement of the trigger stop release member 152 along the trigger actuation surface 162.

Figure 12A:
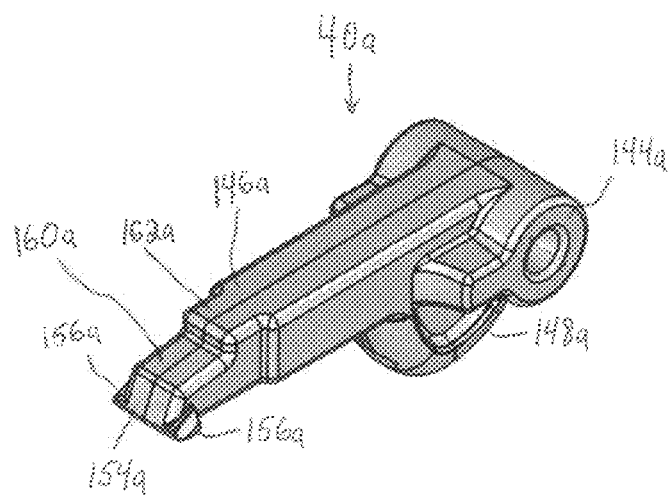
FIG. 12A is a top, perspective view of a trigger stop in accordance with an example of the present disclosure.
Figure 12B:
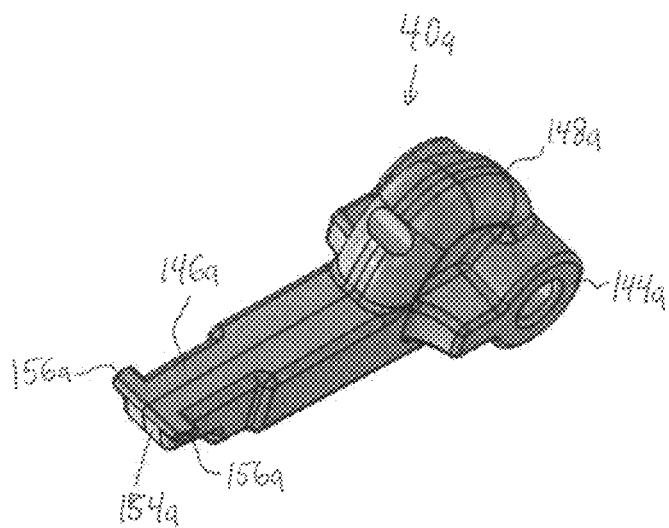
FIG. 12B is a bottom, perspective view of a trigger stop in accordance with an example of the present disclosure.

A non-limiting example embodiment of a trigger stop 40a is shown in FIGS. 12A and 12B. The embodiment of the trigger stop 40a includes a first end 144a, a second end 146a, a dampening cam 148a, a first stop member engagement surface 154a, a trigger latch 156a, a release surface 160a, and a trigger actuation surface 162a. This non-limiting example embodiment of trigger stop 40a can be used in the embodiments of the fastener applicator of the present disclosure, including the embodiments of the fastener applicator shown in FIGS. 6A, 6B and 7A-7E.

With continued reference to FIG. 6A, the lockout mechanism 140a further comprises the ratcheting mechanism 46 that engages when the trigger 32 is moved from the intermediate position toward the actuated position. The ratcheting mechanism 46 is configured to prevent movement of the trigger 32 toward the initial position after the trigger 32 has been moved from the intermediate position toward the actuated position. In some examples, the ratcheting mechanism 46 is actuated when the trigger 32 is moved from the intermediate position toward the actuated position by a predetermined distance. In further examples, the ratcheting mechanism 46 is actuated when the trigger actuation surface 162 of the trigger stop 40 engages the trigger stop release member 152 of the trigger release button 96 as the trigger 32 is moved from the intermediate position toward the actuated position while the trigger release button 96 is pressed. In further examples, the ratcheting mechanism 46 is configured to automatically disengage when the trigger 32 reaches the actuated position to permit movement of the trigger 32 back toward to the initial position.

The ratcheting mechanism 46 comprises a ratchet rod 120 that is selectively engagable with a ratchet lever 128 when the trigger 32 is moved from the intermediate position toward the actuated position. The ratchet rod 120 is movable axially in a distal-to-proximal direction as the trigger 32 is pivoted from the intermediate position (FIG. 7A) toward the actuated position (FIG. 7E). The ratchet rod 120 is linked to the trigger 32 via a coupler 131 (shown in FIG. 5). The ratchet rod 120 can pivot relative to the trigger 32 about the pins 168 (shown in FIG. 5). The ratchet lever 128 is movable between an initial position (FIG. 7A) and an engaged position (FIGS. 7D-7E). In some examples, the ratchet lever 128 is pivotable about a ratchet pivot pin 132. The ratchet lever 128 may be biased in a direction toward the initial position by a ratchet lever biasing mechanism, such as a ratchet lever spring 134. Moving the trigger 32 from the initial position (FIG. 7A) toward the actuated position (FIG. 7E) results in an axial movement of the pull rod 78 in a proximal direction of the longitudinal axis 118 of the shaft 14 and an axial movement of the ratchet rod 120 in the proximal direction.

With continued reference to FIG. 6A, the proximal end of the ratchet rod 120 has one or more teeth 130 that interact with a ratchet lever 128. Movement of the ratchet rod 120 in the proximal direction due to movement of the trigger 32 from the intermediate position toward the actuated position engages the proximal end of the ratchet rod 120 with the ratchet lever 128. The initial contact between the proximal end of the ratchet rod 120 with the ratchet lever 128 displaces the ratchet lever 128 from the disengaged position toward the engaged position by pivoting the ratchet lever 128 against the ratchet lever spring 134.

The one or more teeth 130 of the ratchet rod 120 engage a locking tip 136 of the ratchet lever 128 when the trigger 32 is moved from the intermediate position toward the actuated position to prevent movement of the trigger 32 from the intermediate position toward the initial position. The ratchet rod 120 can include any number of teeth such that the trigger 32 can be progressively closed (i.e., brought into approximation of the handle 32) by more fully driving the ratchet rod 120 under the ratchet lever 128 in the direction of closure for the trigger 32 (e.g., from the configuration of FIG. 7A to the configuration of FIG. 7E).

In some examples, the ratchet lever 128 may engage the ratchet rod 120 prior to the trigger 32 reaching the actuated position to prevent reverse movement of the trigger from the actuated position toward the initial position. For example, the proximal end of the ratchet rod 120 can contact a ratchet lever engagement surface 138 at a proximal end of the ratchet lever 128. The ratchet lever engagement surface 138 may be angled such that proximal movement of the ratchet rod 120 pivots the ratchet lever 128. In some examples, the ratchet lever 128 can be locked due to engagement of one or more locking tabs 139 on the ratchet lever 128 with at least a portion of the housing 36. In some examples, the one or more locking tabs 139 may be laterally deflectable between a first position, wherein the ratchet lever 128 can freely pivot about the ratchet pivot pin 132, and a second position, wherein the ratchet lever 128 is locked relative to the housing 36. The one or more locking tabs 139 may strike the housing 36, thus causing a loud click to audibly alert the user that the trigger 32 has reached the actuated position and that jaws 18, 20 have been closed. This audible confirmation indicates to the user that the fastener 22 has been closed and that the trigger 32 can be released. Once the one or more locking tabs 139 of the ratchet lever 128 engage the housing 36, the ratchet lever 128 is locked in a disengaged state relative to the ratchet rod 120.

Figure 13A:
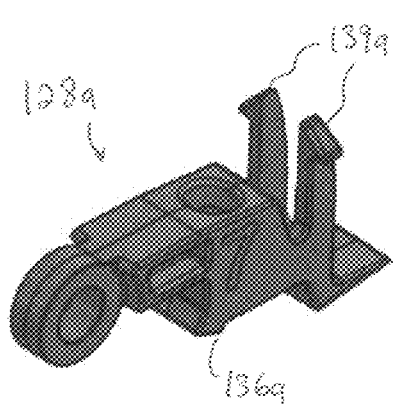
FIG. 13A is a top, perspective view of a ratchet lever in accordance with an example of the present disclosure.
Figure 13B:
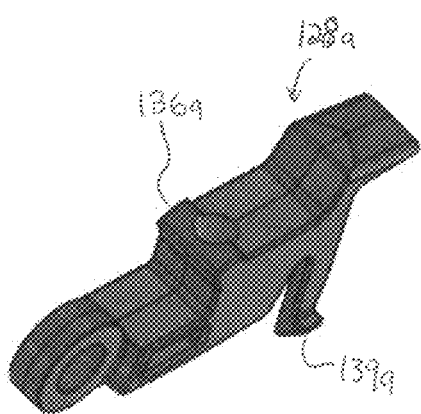
FIG. 13B is a bottom, perspective view of a ratchet lever in accordance with an example of the present disclosure.

A non-limiting example embodiment of a ratchet lever 128a is shown in FIGS. 13A and 13B, and ratchet lever 128a includes a locking tip 136a and two locking tabs 139a. This non-limiting example embodiment of ratchet lever 128a can be used in the embodiments of the fastener applicator of the present disclosure, including the embodiments of the fastener applicator shown in FIGS. 6A, 6B and 7A-7E.

Figure 6B:
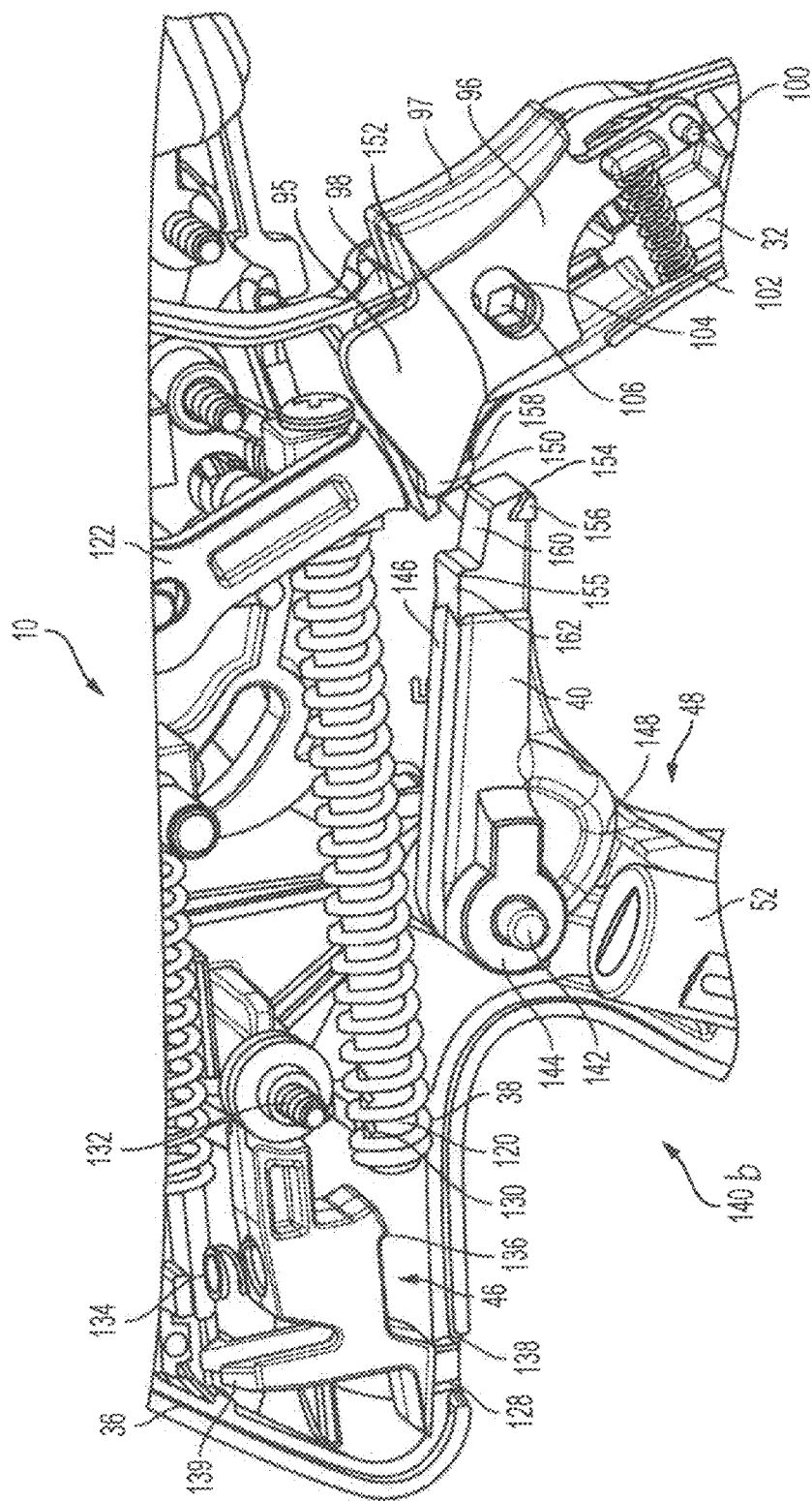
FIG. 6B is a detailed perspective view of a trigger release button and trigger stop of a fastener applicator in accordance with another example of the present disclosure.

With reference to FIG. 6B, the fastener applicator 10 is shown with a lockout mechanism 140b in accordance with another example of the present disclosure. The components of the lockout mechanism 140b shown in FIG. 6B are substantially similar to the components of the lockout mechanism 140a described herein with reference to FIG. 6A. As the previous discussion regarding the lockout mechanism 140a generally shown in FIG. 6A is applicable to the lockout mechanism 140b shown in FIG. 6B, only the relative differences between the two lockout mechanisms are discussed hereinafter.

With continued reference to FIG. 6B, the trigger release button 96 has a stop member 150 positioned at a second free end 95 of the trigger release button 96 and configured for engaging at least a portion of the trigger stop 40 only when the trigger 32 is moved to the intermediate position. Unlike the trigger release button 96 and the trigger stop 40 shown in FIG. 6A, the trigger release button 96 and the trigger stop 40 of FIG. 6B are configured to allow movement of the trigger 32 from the initial position even if the trigger release button 96 is pressed before the trigger 32 is moved from the initial position. In other words, if the trigger release button 96 is pressed and held, the trigger 32 can pass through the intermediate position without stopping and ultimately to the actuated position.

With continued reference to FIG. 6B, the trigger stop release member 152 of the trigger release button 96 is configured for engaging at least a portion of the trigger stop 40 when the trigger 32 is positioned in the intermediate position between the initial position and the actuated position. Pressing the trigger release button 96 when the trigger 32 is in the intermediate position engages the trigger stop release member 152 with the trigger stop 40 to unlock the trigger stop 40 and permit movement of the trigger 32 from the intermediate position toward the actuated position. In some examples, pressing the trigger release button 96 when the trigger 32 is in the initial position engages the trigger stop release member 152 with the trigger stop 40 to unlock the trigger stop 40 and permit movement of the trigger 32 from the initial position toward the actuated position, thereby bypassing the locking of the trigger 32 in the intermediate position.

With continued reference to FIG. 6B, the first stop member engagement surface 154 of the trigger stop 40 is configured as a substantially planar portion at a terminal portion of the second end 146 of the trigger stop 40. Similarly, the second stop member engagement surface 155 may be substantially planar, as opposed to the recessed configuration shown in FIG. 6A. Pressing the trigger release button 96 prior to moving the trigger 32 from the intermediate position toward the actuated position engages the trigger stop release member 152 with the second stop member engagement surface 155 and the trigger actuation surface 162 of the trigger stop 40 to unlock the trigger stop 40 and permit movement of the trigger 32 toward the actuated position.

Having described the structure of the fastener applicator 10, a method of using the fastener applicator 10 to close the fastener 22 over the tissue structure will now be described with reference to FIGS. 7A-8D and 10A-10C. With initial reference to FIG. 7A, the fastener applicator 10 is shown in an initial or as-delivered configuration, wherein the trigger 32 is positioned in the initial position and the jaws 18, 20 (shown in FIG. 8A) are in an open configuration to receive the fastener 22 therebetween. After the fastener 22 is advanced over the tissue structure, such as the LAA, the jaws 18, 20 are closed by manually moving the trigger 32 toward the handle 34 in the direction of arrow A in FIG. 7B. The trigger 32 can be moved toward the handle 34 from the initial position (FIG. 7A) by directing a proximally-directed force in the direction of arrow A on a distal side 110 of the trigger 32.

Figure 8A:
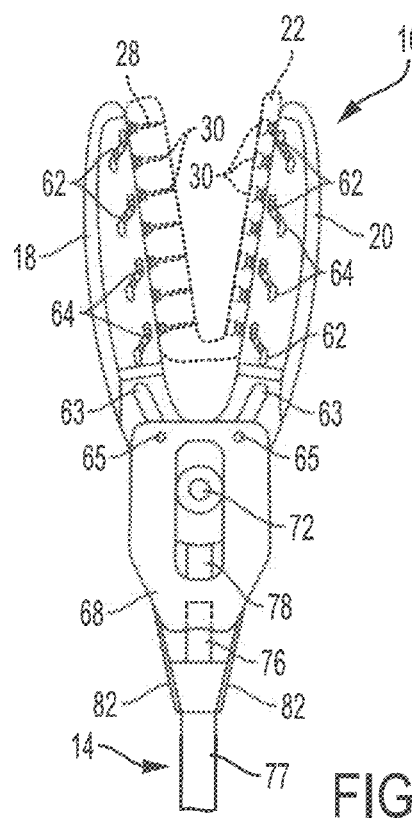
FIGS. 8A-8D illustrate the movement of a jaw assembly and engagement thereof with a tissue closure device according to an example of the present disclosure.
Figure 8B:
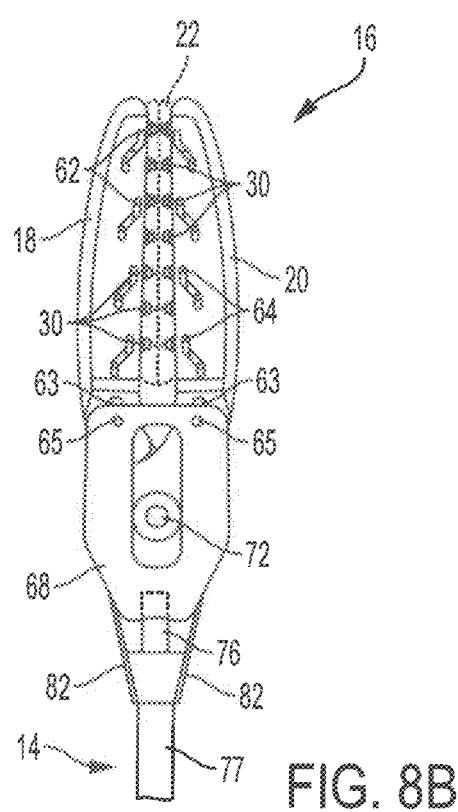

Closing the trigger 32 with respect to the handle 34, that is, pivoting about the trigger pivot pin 44 from the initial position of the trigger 32 (shown in FIG. 10A or FIG. 7A), draws the pull rod 78 proximally toward a proximal end of the shaft 14 relative to the clamp tube 76, which in turn closes the jaws 18, 20 (FIG. 8B). The trigger 32 can be moved in a proximal direction to close the jaws 18, 20 or distally to open the jaws 18, 20 during positioning of the fastener 22 relative to the tissue structure provided that the trigger 32 is not advanced past the intermediate position. This allows the user to carefully position the fastener 22 relative to the tissue structure without closing the fastener 22.

Figure 7B:
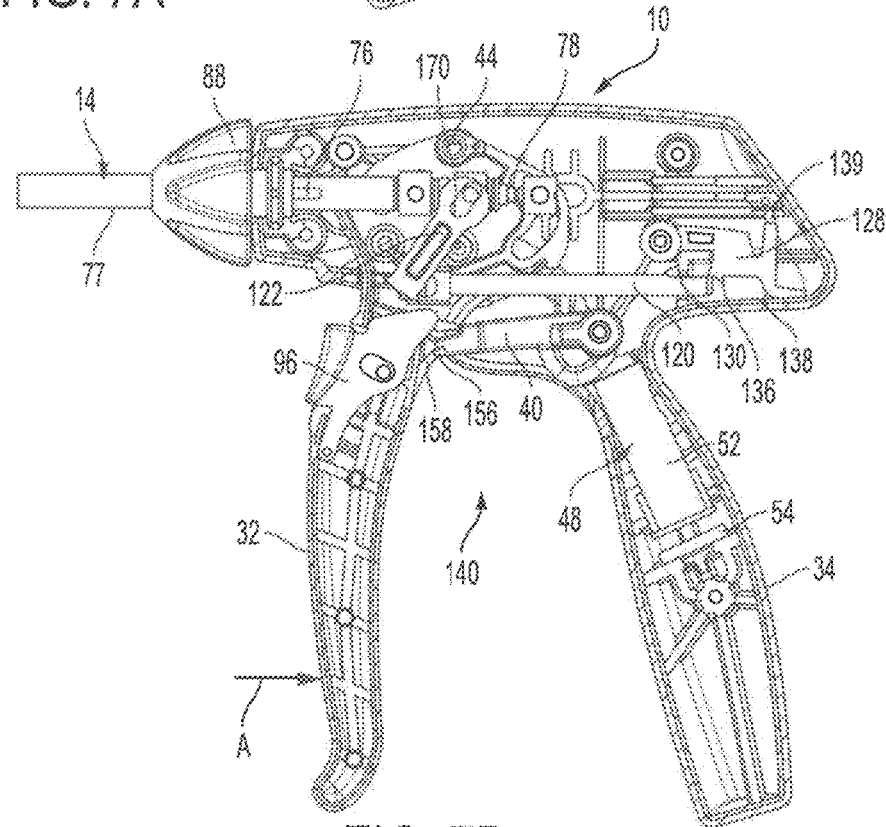
FIG. 7B is a side view of the trigger assembly of the fastener applicator shown in FIG. 1, showing the trigger in a decision or intermediate position and a release button in a first position.
Figure 7C:
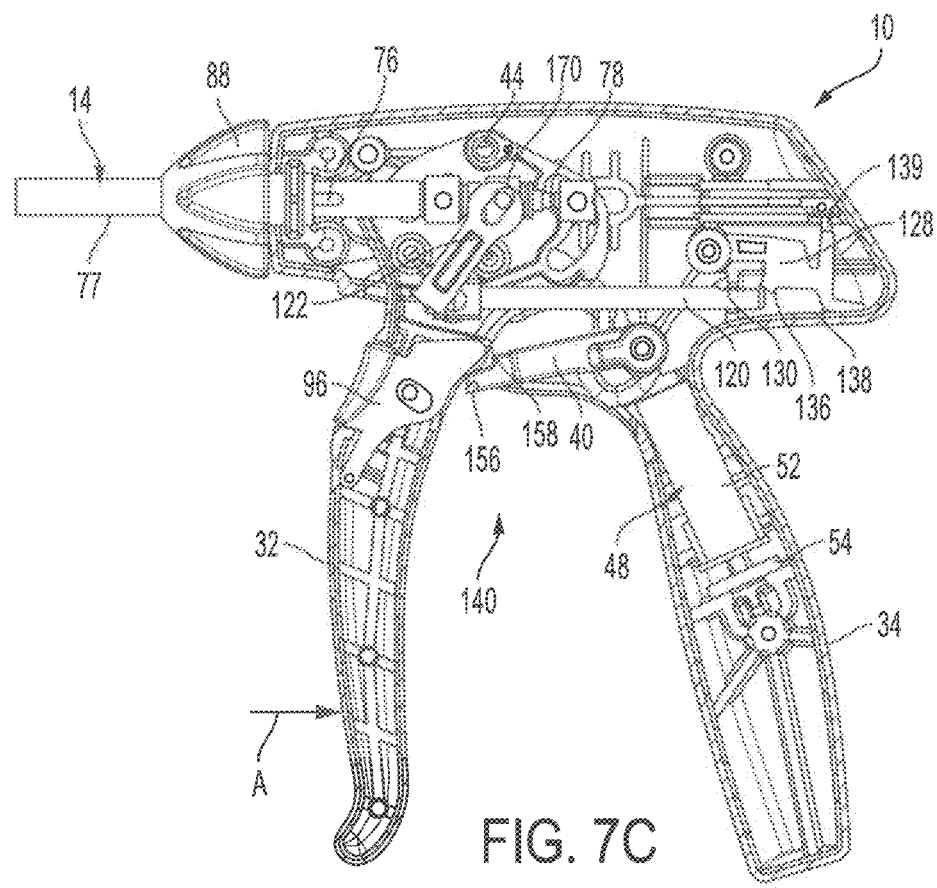
FIG. 7C is a side view of the trigger assembly of the fastener applicator shown in FIG. 1, showing the trigger in a decision or intermediate position with the release button moved from the first position to a second position.
Figure 7D:
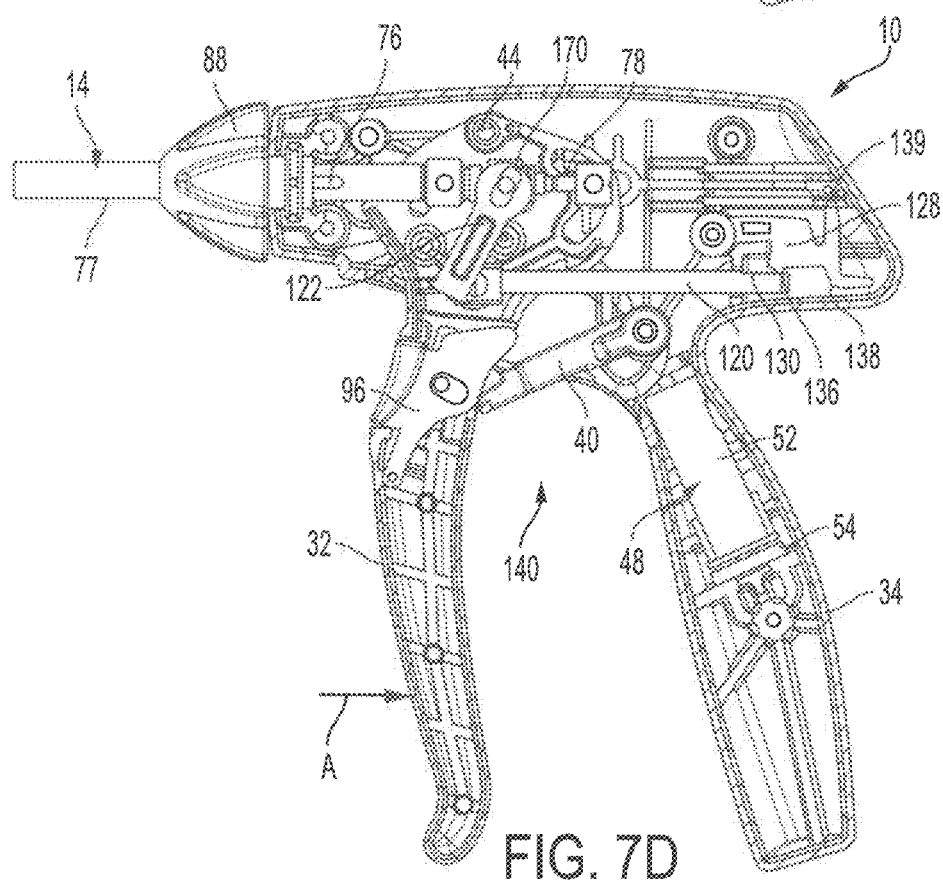
FIG. 7D is a side view of the trigger assembly of the fastener applicator shown in FIG. 1, showing the trigger in a position between the intermediate position and the actuated position.
Figure 7E:
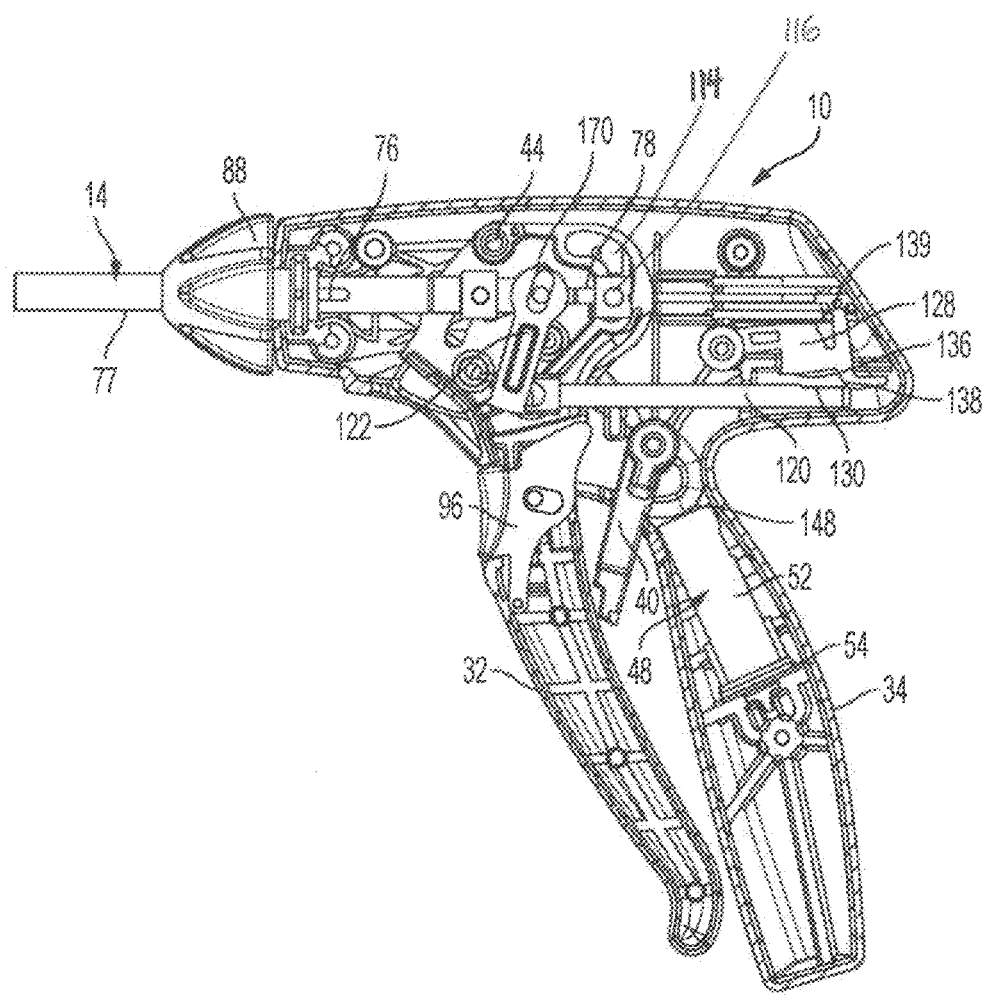
FIG. 7E is a side view of the trigger assembly of the fastener applicator shown in FIG. 1, showing the trigger in a final or actuated position.

With reference to FIG. 7B, the trigger 32 is shown in the intermediate position, wherein the trigger 32 is temporarily locked relative to the handle 34 due to engagement of a trigger latch 156 on the trigger stop 40 with a trigger catch 158 on the trigger 32. When the trigger 32 is moved to the intermediate position and locked therein, further movement of the trigger 32 toward the initial position or the actuated position is prevented without further user input via the trigger release button 96. With the trigger 32 locked in the intermediate position, the jaws 18, 20 are closed in a "preview" position, wherein the legs 26 of the fastener 22 are brought toward one another to capture the tissue structure therebetween without engaging the tissue penetrating fasteners 30 (FIG. 8A). This allows the user to preview the positioning of the fastener 22 relative to the tissue structure without closing the fastener 22.

If repositioning of the fastener 22 relative to the tissue structure is necessary, the trigger 32 can be unlocked by pressing the trigger release button 96 to disengage the trigger latch 156 from the trigger catch 158 (FIG. 7C). By pressing the trigger release button 96, at least a portion of the trigger release button 96, such as the stop member 150 of the trigger release button 96, contacts at least a portion of the trigger stop 40, such as the release surface 160 on the trigger stop 40, to move the trigger stop 40 and displace the trigger latch 156 from contact with the trigger catch 158 on the trigger 32. The trigger 32 can then be moved distally relative to the handle 34 due to a restoring force of the trigger spring 42 (shown in FIG. 3). Movement of the trigger 32 toward the initial position and away from the handle 34 opens the jaws 18, 20 to allow repositioning of the fastener 22.

Referring now to FIG. 7D, if the fastener applicator 10 is oriented such that the fastener 22 is arranged at a desired position relative to the tissue structure, the trigger 32 is unlocked from the intermediate position by pressing the trigger release button 96 to disengage the trigger latch 156 from the trigger catch 158. The trigger 32 can then be advanced proximally toward the handle 34 by moving the trigger 32 in the direction of arrow A. Closing the trigger 32 with respect to the handle 34 moves the trigger stop 40 from a first position (FIG. 7C) to a second position (FIG. 7E) relative to the handle 34 to allow further proximal movement of the trigger 32 toward the actuated position.

Figure 10C:
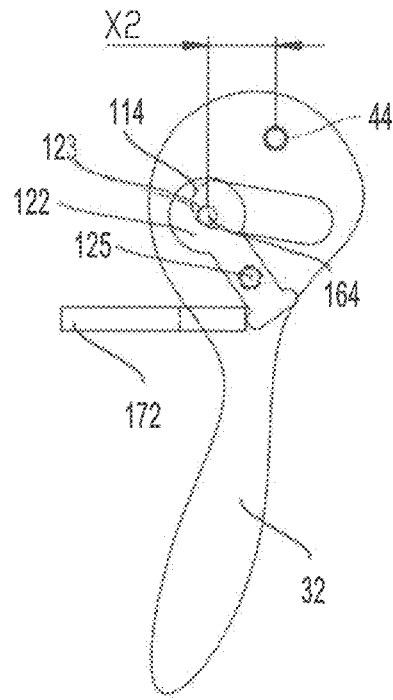

Closing the trigger 32 with respect to the handle 34 also proximally retracts the ratchet rod 120 which is linked to the trigger 32. With reference to FIG. 10C, with the trigger 32 positioned in the actuated position, the trunnion 116 moves to a proximal end of the trigger slot 114 such that a center of the trunnion 116, and therefore the opening 123, is spaced apart proximally from a center of the trigger pivot pin 44 by a second predetermined distance X2 that is larger than the first predetermined distance X1 shown in FIG. 10A. The trigger sub lever 122 is oriented such that its terminal end contacts the ratchet rod 120 and advances the ratchet rod 120 in a proximal direction. Proximal movement of the ratchet rod 120 due to movement of the trigger 32 past the intermediate position engages the teeth 130 of the ratchet rod 120 with the locking tip 136 of the locking lever 128, thereby activating the ratcheting mechanism 46. Once the ratcheting mechanism 46 is engaged, retraction of the trigger 32 in a direction toward the initial position (FIG. 7A) is prevented. In this manner, the user is committed to closing the fastener 22 on the tissue structure by fully engaging the trigger 32 toward the actuated position.

Figure 8C:
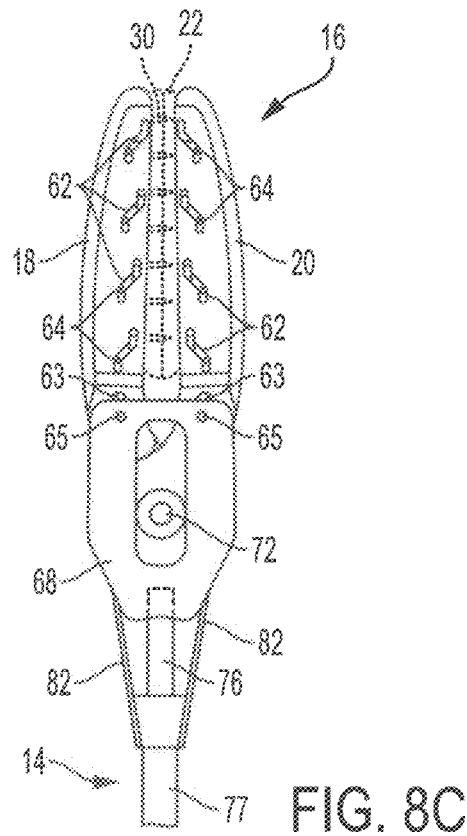

Closure of the trigger 32 from the intermediate position toward the actuated position further draws the pull rod 78 proximally toward a proximal end of the shaft 14 relative to the clamp tube 76. The ejection tube 77 pulls at least one tendon 82 to retract the comb studs 66. When the jaws 18, 20 are closed, the stud combs 66 engage the tissue penetrating fasteners 30 so that they engage and lock with each other, thus closing the two legs 26 of the fastener 22, as shown in FIG. 8C.

As the trigger 32 is advanced from the intermediate position toward the actuated position, the trigger stop 40 is deflected by the trigger 32 from the first position (FIG. 7A) toward the second position (FIG. 7E). As the trigger stop 40 moves from the first position to the second position, the dampening cam 148 of the trigger stop 40 contacts the damper plunger 52 of the dampening mechanism 48, thereby compressing the dampening spring 50 (shown in FIG. 3). As the dampening plunger 52 is compressed against the restoring force of the dampening spring 50, the dampening plunger 52 engages the damper 54 (shown in FIG. 7E), which provides resistance to the compressive force directed to the trigger 32 in the direction of arrow A. As described herein, the dampening cam 148 on the trigger stop 40 and the dampening mechanism 48 are configured such that the user feels a substantially constant reactive force from the trigger 32 during movement of the trigger 32 from the intermediate position toward the final position regardless of the position of the trigger 32 during its stroke between the intermediate position and the actuated position. For example, the user may perceive a substantially constant reactive force from the trigger 32 while moving the trigger 32 toward the handle 34 in the direction of arrow A, thereby requiring a substantially constant compressive force on the trigger 32 during movement of the trigger 32 from the intermediate position toward the actuated position.

Figure 8D:
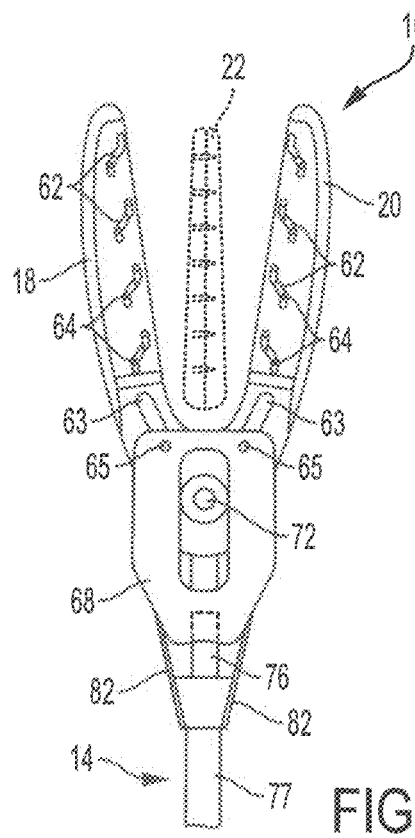

Referring now to FIG. 7E, the trigger 32 is moved to the actuated position to release the trigger 32 from the ratcheting mechanism 46 and allow retraction of the trigger 32 toward the initial position. As described herein, the proximal end of the ratchet rod 120 contacts a ratchet lever disengagement surface 138 at a proximal end of the ratchet lever 128, which lifts the ratchet lever 128 from the ratchet rod 120 and prevents reengagement with the ratchet rod 120 due to interaction of the one or more locking tabs 139 on the ratchet lever 128 with at least a portion of the housing 36. The jaws 18, 20 may be opened by releasing manual compression on the trigger 32, thereby allowing the trigger spring 38 and the main spring 42, which was compressed during closure of the trigger 32 to push the ratchet rod 120 distally forward, opening the jaws 18, 20 and leaving the fastener 22 in place (FIG. 8D).

Figure 9:
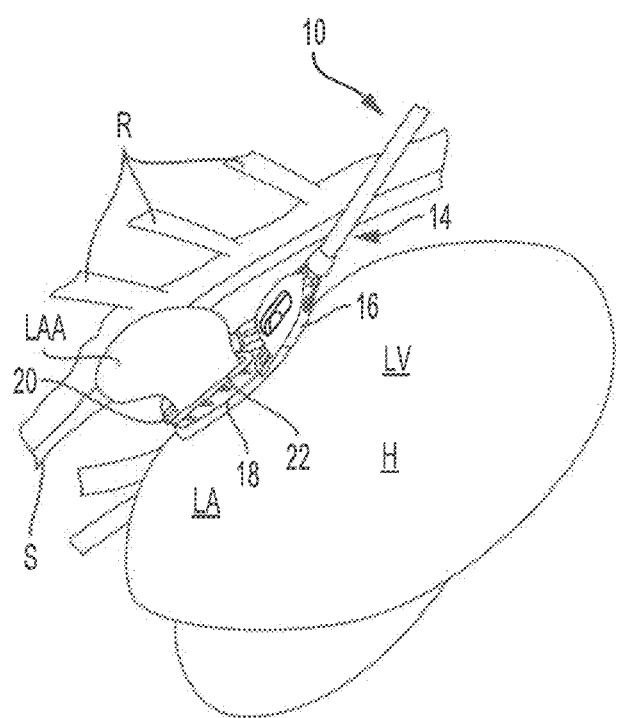
FIG. 9 illustrates use of the fastener applicator according to an example of the present disclosure, wherein the fastener applicator is used for closing a tissue closure device over a LAA.

Referring now to FIG. 9, one specific example of use is illustrated. In this example, the fastener applicator 10 is used to deliver a fastener 22 over the base of a left atrial appendage LAA in an open chest, beating heart procedure. The sternum S is opened, spreading the ribs R to provide a working space over the heart H. After opening the pericardial sack, the heart H may be lifted and turned, for example using a sheet of gauze or other material which is placed behind the heart, to expose the left atrial appendage LAA within the opening as shown in FIG. 9. After the left atrial appendage LAA is exposed, the jaws 18, 20 of the fastener applicator 10 are placed around the base of the left atrial appendage LAA by manipulating the shaft 12. Once the jaws 18, 20 properly position the fastener 22 about the base of the left atrial appendage LAA, the jaws 18, 20 are actuated and the fastener 22 is deployed as described previously.

Although the invention has been described in detail for the purpose of illustration based on what is currently considered to be the most practical and preferred examples, it is to be understood that such detail is solely for that purpose and that the invention is not limited to the disclosed examples, but, on the contrary, is intended to cover modifications and equivalent arrangements that are within the spirit and scope of the appended claims. For example, it is to be understood that the present invention contemplates that, to the extent possible, one or more features of any example can be combined with one or more features of any other example.

The invention claimed is:

1. A surgical applicator for a fastener, the surgical applicator comprising:
a handle;
a trigger movable relative to the handle between an initial position, an actuated position, and an intermediate position between the initial position and the actuated position; and
a lockout mechanism movable relative to the trigger between a locked position and an unlocked position, the lockout mechanism comprising a release button connected to the trigger, the release button movable between a first position and a second position relative to the trigger and wherein the release button is positioned relative to the trigger such that the release button is configured to be operated by a user's index finger, and
the lockout mechanism operatively arranged to:
lock the trigger in the intermediate position when the trigger is moved from the initial position toward the actuated position such that movement of the trigger in a forward direction and a backward direction is prevented when a pressure is applied to the trigger; and
permit movement of the trigger from the intermediate position toward the initial position or the actuated position when the lockout mechanism is moved from the locked position to the unlocked position.

2. The surgical applicator of claim 1, wherein the lockout mechanism is further operatively arranged to permit movement of the trigger from the initial position to the actuated position when the lockout mechanism is moved from the locked position to the unlocked position prior to movement of the trigger from the initial position.

3. The surgical applicator of claim 1, wherein the trigger is movable relative to the handle from the initial position with application of a compressive force on the trigger in a direction toward the handle.

4. The surgical applicator of claim 1, wherein the trigger has a distal side opposite a proximal side facing the handle, and wherein at least a portion of the lockout mechanism is positioned on the distal side of the trigger.

5. The surgical applicator of claim 1, wherein the lockout mechanism further comprises:
a trigger stop connected to the handle, the trigger stop movable between a first position and a second position relative to the handle.

6. The surgical applicator of claim 5, wherein the release button is pivotally movable relative to the trigger.

7. The surgical applicator of claim 5, wherein the release button is linearly movable in a direction lateral relative to the trigger.

8. The surgical applicator of claim 5, wherein the release button is biased to the first position by a release button biasing member.

9. The surgical applicator of claim 5, wherein the trigger stop is biased to the first position by a trigger stop biasing member.

10. The surgical applicator of claim 5, wherein movement of the trigger from the initial position toward the actuated position engages the trigger with the trigger stop to automatically lock the trigger in the intermediate position.

11. The surgical applicator of claim 5, wherein movement of the release button from the first position to the second position when the trigger is in the intermediate position permits disengagement of the trigger from the trigger stop.

12. The surgical applicator of claim 1, further comprising a ratcheting mechanism that engages the trigger when the trigger is moved from the intermediate position toward the actuated position to prevent movement of the trigger toward the initial position.

13. The surgical applicator of claim 12, wherein the ratcheting mechanism disengages from the trigger when the trigger is moved to the actuated position.

14. The surgical applicator of claim 12, wherein the ratcheting mechanism comprises a ratchet rod and a ratchet that is engaged with the ratchet rod when the trigger is moved from the intermediate position toward the actuated position.

15. The surgical applicator of claim 12, wherein the ratcheting mechanism is actuated when the trigger is moved from the intermediate position toward the actuated position by a predetermined distance.

16. The surgical applicator of claim 1, further comprising a jaw assembly selectively movable between an open position and a closed position via movement of the trigger from the initial position to the actuated position.

17. The surgical applicator of claim 16, wherein the jaw assembly comprises a pair of jaws movably attached to one another, each jaw having a pair of lateral sides with a plurality of lateral slots extending through each lateral side.

18. The surgical applicator of claim 17, wherein an outer surface of at least one of the lateral sides of each jaw has a recess.

19. The surgical applicator of claim 18, wherein the recess receives a cover element that encloses at least a portion of the plurality of lateral slots.

20. The surgical applicator of claim 19, wherein the cover element is adhesively secured in the recess.

21. The surgical applicator of claim 17, wherein the jaws are pivotally attached to one another by a pin.

22. The surgical applicator of claim 1, further comprising a dampening mechanism operatively arranged with the trigger to dampen variations in a compressive force applied on the trigger during movement between the initial position and the actuated position.

23. The surgical applicator of claim 22, wherein the dampening mechanism comprises a spring and a damper.

24. The surgical applicator of claim 1, wherein the release button is positioned on the trigger.

25. A surgical applicator for a fastener, the surgical applicator comprising:
a handle;
a trigger movable relative to the handle between an initial position, an actuated position, and an intermediate position between the initial position and the actuated position; and
a lockout mechanism comprising a release button connected to the trigger and a trigger stop connected to the handle, wherein the release button is movable between a first position and a second position relative to the trigger and wherein the release button is positioned relative to the trigger such that the release button is configured to be operated by a user's index finger, and
wherein movement of the trigger from the initial position toward the actuated position engages the trigger stop with the trigger to lock the trigger in the intermediate position such that movement of the trigger in a forward direction and a backward direction is prevented when a pressure is applied to the trigger, and
wherein movement of the release button relative to the trigger when the trigger is in the intermediate position disengages the trigger from the trigger stop to permit movement of the trigger from the intermediate position toward the initial position or the actuated position.

26. The surgical applicator of claim 25, further comprising a ratcheting mechanism that engages the trigger when the trigger is moved from the intermediate position toward the actuated position to prevent movement of the trigger toward the initial position.

27. The surgical applicator of claim 26, wherein the ratcheting mechanism disengages from the trigger when the trigger is moved to the actuated position.

28. A surgical applicator for a fastener, the surgical applicator comprising:
a handle;
a trigger movable relative to the handle between an initial position, an actuated position, and an intermediate position between the initial position and the actuated position;
an elongate body extending distally from the handle, the elongate body having a distal portion;
a jaw assembly at the distal portion of the elongate body, the jaw assembly selectively movable between an open position, a closed position, and an intermediate position between the open position and the closed position via movement of the trigger; and
a lockout mechanism operatively arranged to:
lock the trigger and the jaw assembly in the intermediate position when the trigger is moved from the initial position toward the actuated position such that movement of the trigger in a forward direction and a backward direction is prevented when a pressure is applied to the trigger; and
permit movement of the trigger from the intermediate position toward the initial position or the actuated position to move the jaw assembly from the intermediate position toward the open position or the closed position, respectively,
wherein the lockout mechanism comprises a release button connected to the trigger, the release button movable between a first position and a second position relative to the trigger and wherein the release button is positioned relative to the trigger such that the release button is configured to be operated by a user's index finger.

29. A method of operating a fastener applicator, the method comprising:
moving a trigger of the fastener applicator from an initial position toward an actuated position by applying a compressive force on the trigger in a direction toward a handle of the fastener applicator;
closing a jaw assembly of the fastener applicator from an open position toward a closed position via movement of the trigger;
locking the trigger and the jaw assembly in an intermediate position with a lockout mechanism, such that movement of the trigger in a forward direction and a backward direction is prevented when a pressure is applied to the trigger, wherein the lockout mechanism comprises a release button connected to the trigger, the release button movable between a first position and a second position relative to the trigger and wherein the release button is positioned relative to the trigger such that the release button is configured to be operated by a user's index finger, and;

moving the lockout mechanism from a locked position to an unlocked position;

moving the trigger from the intermediate position toward the actuated position; and closing the jaw assembly from the intermediate position to the closed position via movement of the trigger.

30. The method of claim 29, wherein closing the jaw assembly to the closed position closes a fastener from an unfixed to a fixed position.

31. The method of claim 29, further comprising blocking the trigger via a ratcheting mechanism from movement toward the initial position after the trigger is moved from the intermediate position toward the actuated position.

32. The method of claim 29, wherein the jaw assembly moves from the closed position toward the open position after the trigger is moved to the actuated position.

33. The method of claim 29, further comprising unlocking the trigger when the trigger is moved to the actuated position.

* * * * *